(12) United States Patent
Saito et al.

(10) Patent No.: US 6,825,353 B2
(45) Date of Patent: Nov. 30, 2004

(54) PROCESS FOR PRODUCING QUINOLONECARBOXYLIC ACIDS AND INTERMEDIATES THEREOF

(75) Inventors: Tatsuru Saito, Edogawa-ku (JP); Toshiaki Jouno, Edogawa-ku (JP); Yuichiro Tani, Edogawa-ku (JP); Toshifumi Akiba, Edogawa-ku (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 48 days.

(21) Appl. No.: 10/204,550

(22) PCT Filed: Feb. 23, 2001

(86) PCT No.: PCT/JP01/01370

§ 371 (c)(1),
(2), (4) Date: Aug. 22, 2002

(87) PCT Pub. No.: WO01/62734

PCT Pub. Date: Aug. 30, 2001

(65) Prior Publication Data

US 2003/0060631 A1 Mar. 27, 2003

(30) Foreign Application Priority Data

Feb. 25, 2000 (JP) ....................................... 2000-054349
Apr. 13, 2000 (JP) ....................................... 2000-117208

(51) Int. Cl.$^7$ .......................................... C07D 215/56
(52) U.S. Cl. ...................................................... 546/156
(58) Field of Search .......................................... 546/156

(56) References Cited

FOREIGN PATENT DOCUMENTS

| | | |
|---|---|---|
| EP | 0 641 793 A1 | 3/1995 |
| EP | 0 806 421 A1 | 11/1997 |
| EP | 0 911 328 A1 | 4/1999 |
| JP | 11-158150 | 6/1999 |
| JP | 2000-247970 | 9/2000 |
| JP | 2000-319261 | 11/2000 |
| WO | WO 97/19072 | 5/1997 |

OTHER PUBLICATIONS

Toshihiko Yoshida, et al., "Studies on Quinolone Antibacterials. V.[1)] Synthesis and Antibacterial Activity of Chiral 5–Amino–7–(4–substituted–3–amino–1–pyrrolidinyl)–6–fluoro–1, 4–dihydro–8–methyl–4–oxoquinoline–3–carboxylic Acids and Derivatives". Chem. Pharm. Bull., vol. 44, No. 7, pp. 1376–1386, 1996.

Kiyoshi Matsumoto, et al., "High Pressure Synthesis of New Ag$^+$ Ion–Specific Crown Ethers". Tetrahedron Letters, vol. 31, No. 27, pp. 3923–2926, 1990.

Hiyoshizo Kotsuki, et al., "High Pressure Organic Chemistry; XII. A Convenient Synthesis of Aromatic Amines from Activated Aromatic Fluorides." Synthesis, No. 12, pp. 1147–1148, 1990.

Shiro Hashimoto, et al., "Aminolysis of Halogenopyridines at High Pressures" Heterocycles, vol. 27, No. 2, pp. 319–322, 1988.

Primary Examiner—Patricia L. Morris
(74) Attorney, Agent, or Firm—Sughrue Mion, PLLC

(57) ABSTRACT

This invention relates to methods for the efficient production of quinolonecarboxylic acid based synthetic antibacterial agents which are expected for applications such as excellent medicaments and agricultural chemicals and to intermediate compounds to be used therein. According to the present invention, an amine substituent as the 7-position substituent of the quinolonecarboxylic acid derivative can be efficiently introduced.

13 Claims, No Drawings

PROCESS FOR PRODUCING QUINOLONECARBOXYLIC ACIDS AND INTERMEDIATES THEREOF

TECHNICAL FIELD

This invention relates to methods for the efficient production of quinolonecarboxylic acid synthetic antibacterial agents which are expected for applications such as excellent medicaments and agricultural chemicals and to intermediate compounds to be used therein.

BACKGROUND ART

Among quinolone synthetic antibacterial agents useful as antibacterial agents, 5-amino-8-methylquinolonecarboxylic acid derivatives are known to have excellent characteristics. As shown below,

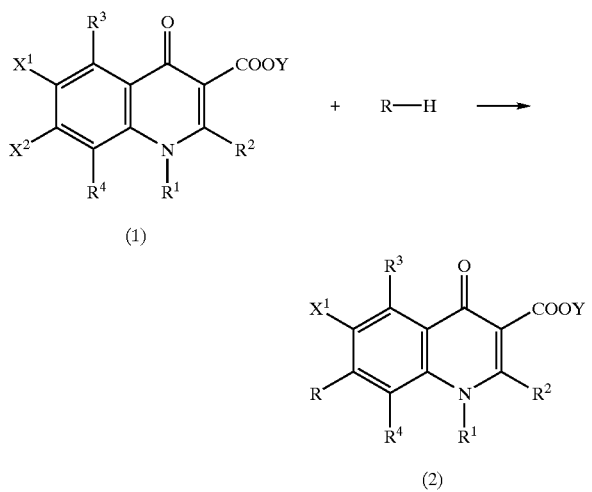

synthesis of such quinolone derivatives is carried out by allowing a compound of formula (1) to react with a basic substituent compound (R—H; which means a compound capable of introducing a basic substituent by a substitution reaction). For example, a method of the following formula:

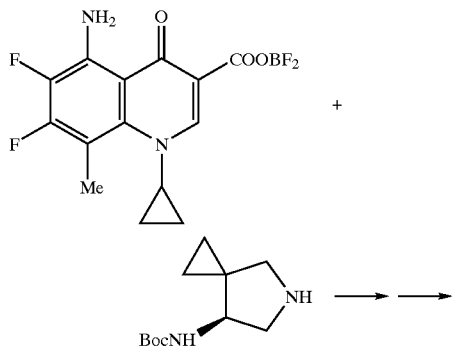

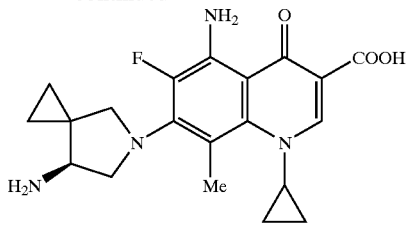

is known, in which a 5-amino-8-methylquinolonecarboxylic acid $BF_2$ chelate [a compound of the formula (1) wherein $R^3=NH_2$, $R^4=Me$ and $Y=BF_2$] is allowed to react with a basic substituent compound in an appropriate solvent in the presence of an appropriate base.

That is, a method in which (S)-7-tert-butoxycarbonylamino-5-azaspiro[2.4]heptane (or its hydrochloride) is allowed to undergo the reaction at 30° C. for 3 to 4 days in dimethyl sulfoxide in the presence of N,N-diisopropylamine and then purified, and the thus obtained crystals are allowed to undergo the reaction by heating in a mixed solvent of methanol-1,2-dichloroethane in the presence of triethylamine and then purified, thereby obtaining 5-amino-7-[(S)-7-tert-butoxycarbonylamino-5-azaspiro[2.4]hept-5-yl]-1-cyclopropyl-6,7-difluoro-1,4-dihydro-8-methyl-4-oxoquinoline-3-carboxylic acid (JP-A-7-309864 and JP-A-8-198819; the term "JP-A" as used herein means an "unexamined published Japanese patent application") However, this is not an industrially satisfactory method because of the low product yield of approximately from 10 to 30%.

Also known is a method in which 5-amino-8-methylquinolonecarboxylic acid [a compound of the formula (1) wherein $R^3=NH_2$, $R^4=Me$ and $Y=H$] and a basic substituent compound are heated in an appropriate solvent in the presence of an appropriate base. That is, a method in which they are stirred and heated at about 100° C. for 87 hours in dimethyl sulfoxide in the presence of triethylamine and then treated, and the thus obtained crystals are purified after carrying out deprotection of amino group in the usual way, thereby obtaining 5-amino-7-[(3S,4S)-3-amino-4-ethyl-1-pyrrolidinyl]-1-cyclo propyl-6,7-difluoro-1,4-dihydro-8-methyl-4-oxoquinoline-3-carboxylic acid (JP-A-8-259561) (the following formula):

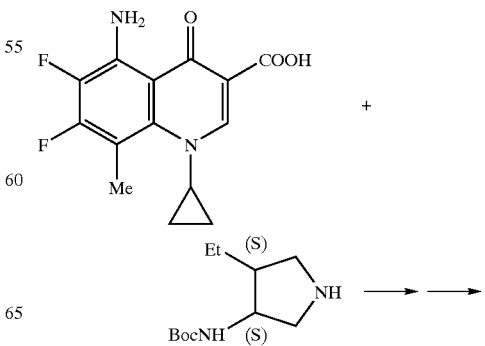

-continued

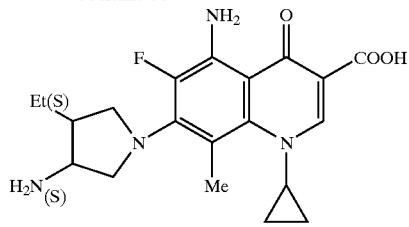

or a method (the following formula):

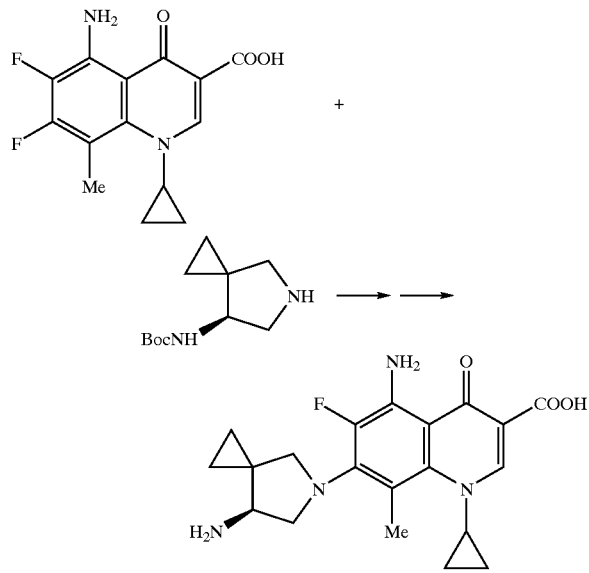

in which 5-amino-7-[(S)-7-amino-5-azaspiro[2.4]hept-5-yl]-1-cyclopropyl-6,7-difluoro-1,4-dihydro-4-methyl-4-oxoquinoline-3-carboxylic acid is obtained (*Chem. Pharm. Bull.*, 44, 1376 (1996)).

However, yields of the final products by these methods are still low, namely 38% and 56% respectively, so that, though the yields are slightly improved in comparison with the foregoing method, they are not industrially satisfactory methods.

Thus, the previous methods for the production of 5-amino-8-methylquinolonecarboxylic acid derivatives were not satisfactory as an industrial production method.

Under such a situation, the present inventors have examined the reason of low yield of the previous reaction of a boron chelate compound of Y=—B(R⁵)₂ in the compound of formula (1) of the invention [(5-amino-1-cyclopropyl-6,7-difluoro-1,4-dihydro-8-methyl-4-oxoquinoline-3-carboxylic acid-O³,O⁴)difluoroboron] with a basic substituent compound.

As a result, it was found that the boron chelate compound easily causes de-chelation on heating. Thus, it was confirmed that de-chelation in the boron chelate quinolone compound preferentially proceeds rather than reacting with a basic substituent compound when the reaction temperature is increased for the purpose of accelerating the reaction (e.g., even by a heating at 30 to 40° C.), while substitution reaction of the compound formed by this de-chelation with the basic substituent compound hardly proceeds at this temperature.

In addition, an open system reaction is carried out under a high temperature (110° C.) condition in the case of the substitution reaction of a carboxylic acid type quinolone compound [a compound in which the 3-position carboxyl group is not modified, such as 5-amino-1-cyclopropyl-6,7-difluoro-1,4-dihydro-8-methyl-4-oxoquinoline-3-carboxylic acid itself] with a pyrrolidine derivative. It was found that, since decomposition reaction of the carboxylic acid quinolone compound itself competitively occurs simultaneously with the substitution reaction by this method, the reaction becomes complex in addition to coloring of the reaction solution. That is, the inventors have considered that yield of the substitution product is reduced due to decomposition of the material compound, and further reduction of the yield occurs because of the difficulty in purifying the final product of interest due to the complex reaction and coloring.

By the way, it is known that the substitution reaction of aromatic halogen compounds with amines sharply progresses when the reaction is carried out in an appropriate solvent under a super-high pressure (cf. *Heterocycles*, 27,319 (1988); *Chem. Lett.*, 1187 (1987); *Synthesis*, 1147 (1990); *Tetrahedron Lett.*, 3923 (1990); *Bull. Chem. Soc. Jpn.*, 64, 42 (1991)). However, such a substitution reaction under a high pressure is mainly a reaction with a monocyclic halogen compound such as benzene, pyrimidine, pyrazine or thiazole, and only a few examples such as benzoxazole and benzothiazole are known as bicyclic halogen compounds but there are no reports on 4-quinolone compounds.

An object of the invention is to provide a method for the efficient production of quinolone compounds having excellent antibacterial activity, pharmacokinetics and safety, particularly a 7-substituted 5-amino-8-methylquinolonecarboxylic acid derivative.

DISCLOSURE OF THE INVENTION

As a result of intensive studies, the present inventors have found that a 5-amino-8-methylquinolonecarboxylic acid derivative can be efficiently provided through inhibition of the decomposition reaction of the quinolone material compound, by carrying out the substitution reaction of a 5-amino-1-substituted-6,7-difluoro-1,4-dihydro-8-methyl-4-oxoquinoline-3-carboxylic acid with a basic substituent compound under a high pressure, thereby accomplishing the invention.

The inventors have further found that the substitution reaction with a basic substituent compound quickly proceeds in the case of a compound in which the 5-position amino group is acylated, and excellent effects are exerted particularly by the reaction under a pressurized condition, thus resulting in the accomplishment of the invention.

Accordingly, the invention relates to a method for producing a compound represented by formula (2):

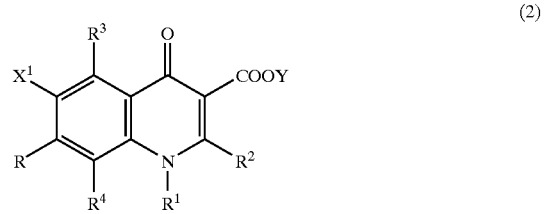

(wherein R¹, R², R³, R⁴, R, X¹ and Y are as defined in the following) which comprises allowing a compound represented by formula (1):

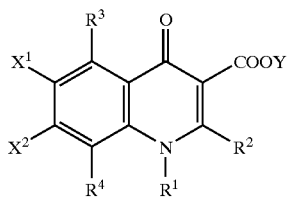

(1)

[wherein $R^1$ represents an alkyl group having from 1 to 6 carbon atoms, an alkenyl group having from 2 to 6 carbon atoms, a halogenoalkyl group having from 1 to 6 carbon atoms, a cyclic alkyl group having from 3 to 6 carbon atoms which may have a substituent, an aryl group which may have a substituent, a heteroaryl group which may have a substituent, an alkoxy group having from 1 to 6 carbon atoms or an alkylamino group having from 1 to 6 carbon atoms, $R^2$ represents a hydrogen atom or an alkylthio group having from 1 to 6 carbon atoms, wherein $R^2$ and $R^1$ may be combined to form a cyclic structure together with the carbon atom and nitrogen atom, to which they are bonded, and this ring may contain a sulfur atom as a constituting atom and may further have an alkyl group having from 1 to 6 carbon atoms as a substituent, $R^3$ represents a hydrogen atom, an amino group, a thiol group, a halogenomethyl group, an alkyl group having from 1 to 6 carbon atoms, an alkenyl group having from 2 to 6 carbon atoms, an alkynyl group having from 2 to 6 carbon atoms or an alkoxy group having from 1 to 6 carbon atoms, wherein the amino group may have one or more substituents selected from the group consisting of a formyl group, an alkyl group having from 1 to 6 carbon atoms and an acyl group having from 2 to 5 carbon atoms, $R^4$ represents a hydrogen atom, an amino group, a halogen atom, a cyano group, a halogenomethyl group, a halogenomethoxy group, an alkyl group having from 1 to 6 carbon atoms, an alkenyl group having from 2 to 6 carbon atoms, an alkynyl group having from 2 to 6 carbon atoms or an alkoxy group having from 1 to 6 carbon atoms, wherein the amino group may have one or more substituents selected from the group consisting of a formyl group, an alkyl group having from 1 to 6 carbon atoms and an acyl group having from 2 to 5 carbon atoms, and $R^4$ and $R^1$ maybe combined to form a cyclic structure together with the carbon atom and nitrogen atom, to which they are bonded, and this ring may contain an oxygen atom, a nitrogen atom or a sulfur atom as a constituting atom and may further have an alkyl group having from 1 to 6 carbon atoms as a substituent, $X^1$ represents a hydrogen atom or a halogen atom, $X^2$ represents a halogen atom, and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidynyl group, a 5-alkyl-2-oxo-1,3-dioxol-4-ylmethyl group, a 3-acetoxy-2-oxobutyl group, an alkyl group having from 1 to 6 carbon atoms, an alkoxymethyl group having from 2 to 7 carbon atoms, a phenylalkyl group composed of an alkylene group having from 1 to 6 carbon atoms and a phenyl group, or a group of the following formula:

—B(R$^5$)$_2$ (wherein $R^5$ represents a fluorine atom or an acyloxy group having from 2 to 7 carbon atoms)]

to react with a nitrogen-containing basic compound represented by the following formula:

R—H (wherein R represents a nitrogen-containing basic substituent in which a nitrogen atom is the binding position), under a pressurized condition in the presence, if necessary, of a base.

The invention also relates to the above production method, wherein the compound of formula (I) is a compound represented by formula (A):

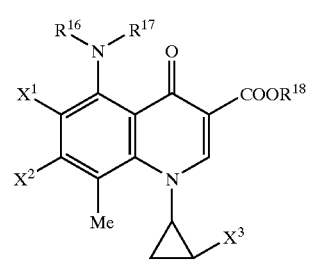

(A)

[wherein $X^1$ is a hydrogen atom or a halogen atom, $X^2$ is a halogen atom, $X^3$ is a hydrogen atom or a halogen atom, $R^{16}$ is a hydrogen atom or an acyl group, $R^{17}$ is an acyl group, and $R^{18}$ is a hydrogen atom, an alkyl group having from 1 to 6 carbon atoms or a boron-containing substituent group represented by the following formula:

—B(R$^5$)$_2$ (wherein $R^5$ is a halogen atom or an acyloxy group)].

It also relates to the above production method wherein $R^5$ is a halogen atom or an alkylcarbonyloxy group;

to the above production method wherein $R^5$ is a fluorine atom or an acetyloxy group;

to the above production method wherein the nitrogen-containing basic compound (R—H) is a compound represented by a formula (B):

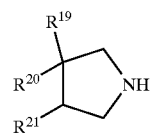

(B)

[wherein each of $R^{19}$ and $R^{20}$ is independently a hydrogen atom, a lower alkyl group or an amino-substituted cyclopropyl group (this amino group may have a substituent or a protective group), or $R^{19}$ and $R^{20}$ may be combined into a group represented by the following formula:

—(CH$_2$)$_2$— and form a spiro cyclic structure together with the pyrrolidine ring, and $R^{21}$ is a halogen atom or an amino group which may have a substituent or a protective group];

to the above production method wherein $R^{19}$ and $R^{20}$ are a group represented by the following formula:

—(CH$_2$)$_2$— and $R^{21}$ is an amino group which may have a substituent or a protective group;

to the above production method wherein the amino group is an amino group of (S)-configuration;
to the above production method wherein $R^{19}$ is a hydrogen atom, $R^{20}$ is an amino-substituted cyclopropyl group (this amino group may have a substituent or a protective group) and $R^{21}$ is a halogen atom;
to the above production method wherein $R^{21}$ is a fluorine atom; to the above production method wherein $R^{20}$ and $R^{21}$ are in cis-form; and to the above production method wherein $R^{20}$ is (R)-configuration and $R^{21}$ is (S)-configuration.

The invention also relates to a compound represented by formula (A):

(A)

[wherein $X^1$ represents a hydrogen atom or a halogen atom, $X^2$ represents a halogen atom, $X^3$ represents a hydrogen atom or a halogen atom, $R^{16}$ represents a hydrogen atom or an acyl group, $R^{17}$ represents an acyl group, and $R^{18}$ represents a hydrogen atom, an alkyl group having from 1 to 6 carbon atoms or a boron-containing substituent represented by the following formula:

—$B(R^5)_2$ (wherein $R^5$ represents a halogen atom or an acyloxy group)], and further relates to the following related compounds.

The above compound wherein $R^{16}$ is a hydrogen atom and $R^{17}$ is an acyl group;
each of the above compounds wherein $R^{17}$ is an acetyl group;
each of the above compounds wherein $X^1$ and $X^2$ are a fluorine atoms;
each of the above compounds wherein $R^{18}$ is a hydrogen atom; a compound represented by formula (C-1):

(C-1)

[wherein $X^1$ represents a hydrogen atom or a halogen atom, $X^3$ represents a hydrogen atom or a halogen atom, each of $R^{19}$ and $R^{20}$ independently represents a hydrogen atom, a lower alkyl group or an amino-substituted cyclopropyl group (this amino group may have a substituent or a protective group), or $R^{19}$ and $R^{20}$ maybe combined into a group represented by the following formula

—$(CH_2)_2$— and form a spiro cyclic structure together with the pyrrolidine ring, and $R^{21}$ represents a halogen atom or an amino group which may have a substituent or a protective group];

the above compound wherein $R^{19}$ and $R^{20}$ are a group represented by the following formula:

—$(CH_2)_2$— and $R^{21}$ is an amino group which may have a substituent or a protective group;
the above compound wherein the amino group is an amino group of (S)-configuration;
the above compound wherein $R^{19}$ is a hydrogen atom, $R^{20}$ is an amino-substituted cyclopropyl group (this amino group may have a substituent or a protective group) and $R^{21}$ is a halogen atom;
the above compound wherein $R^{21}$ is a fluorine atom;
the above compound wherein $R^{20}$ and $R^{21}$ are in cis-form;
the above compound wherein $R^{20}$ is (R)-configuration and $R^{21}$ is (S)-configuration;
a compound represented by formula (C-2):

(C-2)

[wherein $X^1$ represents a hydrogen atom or a halogen atom, $X^3$ represents a hydrogen atom or a halogen atom, $R^{16}$ represents a hydrogen atom or an acyl group, $R^{17}$ represents an acyl group, $R^{18}$ represents a hydrogen atom, an alkyl group having from 1 to 6 carbon atoms or a boron-containing substituent represented by the following formula:

—$B(R^5)_2$ (wherein $R^5$ represents a halogen atom or an acyloxy group), each of $R^{22}$ and $R^{23}$ independently represents a hydrogen atom, a lower alkyl group or an amino-substituted cyclopropyl group (this amino group may have a substituent), or $R^{22}$ and $R^{23}$ may be combined into a group represented by the following formula:

—$(CH_2)_2$— and form a spiro cyclic structure together with the pyrrolidine ring, and $R^{23}$ represents a halogen atom or an amino group which may have a substituent];
the above compound wherein $R^{22}$ and $R^{23}$ are a group represented by the following formula:

—$(CH_2)_2$— and $R^{24}$ is an amino group which may have a substituent; the above compound wherein the amino group is an amino group of (S)-configuration;
the above compound wherein $R^{22}$ is a hydrogen atom, $R^{23}$ is an amino-substituted cyclopropyl group (this amino group may have a substituent) and $R^{24}$ is a halogen atom;
the above compound wherein $R^{24}$ is a fluorine atom;
the above compound wherein $R^{23}$ and $R^{24}$ are in cis-form;
the above compound wherein $R^{23}$ is (R)-configuration and $R^{24}$ is (S)-configuration;
the above compound wherein $R^{16}$ is a hydrogen atom and $R^{17}$ is an acyl group;

the above compound wherein $R^{17}$ is an acetyl group;
each of the above compounds wherein $X^1$ and $X^3$ are fluorine atoms; and
each of the above compounds wherein $R^{18}$ is a hydrogen atom.

The production method of the invention is characterized in that the following substitution reaction is carried out under a pressurized condition:

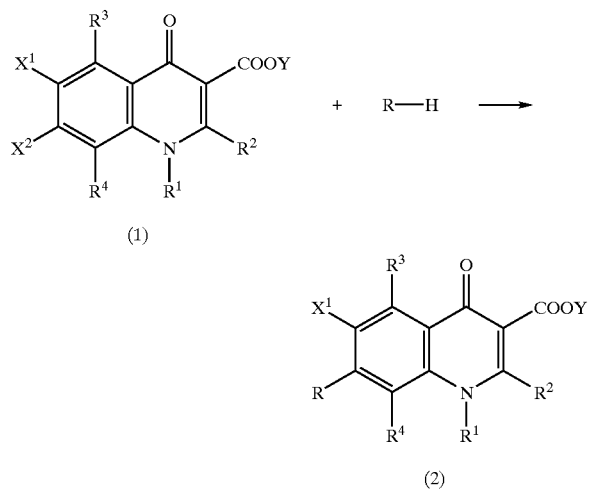

(wherein $R^1$, $R^2$, $R^3$, $R^4$, $R^5$, $R^6$, R, $X^1$, $X^2$ and Y are as defined in the foregoing).

Firstly, substituent groups of the compound represented by the formula (1) or (2) are described.

The substituent $R^1$ is an alkyl group having from 1 to 6 carbon atoms, an alkenyl group having from 2 to 6 carbon atoms, a halogenoalkyl group having from 1 to 6 carbon atoms, a cyclic alkyl group having from 3 to 6 carbon atoms having a substituent, an aryl group which may have a substituent, a heteroaryl group which may have a substituent, an alkoxy group having from 1 to 6 carbon atoms or an alkylamino group having from 1 to 6 carbon atoms.

In this case, an ethyl group is particularly preferable as the alkyl group having from 1 to 6 carbon atoms. A vinyl group or a 1-isopropenyl group is preferable as the alkenyl group having from 2 to 6 carbon atoms. A 2-fluoroethyl group is preferable as the halogenoalkyl group having from 1 to 6 carbon atoms. A halogen atom is preferable as the substituent group of the cyclic alkyl group having a substituent, and a fluorine atom is particularly preferable as the halogen atom.

Examples of the aryl group which may have a substituent include phenyl groups which may have from 1 to 3 substituents selected from the group consisting, for example, of halogen atoms such as a fluorine atom, a chlorine atom and a bromine atom, a hydroxyl group, an amino group, a nitro group, an alkyl group having from 1 to 6 carbon atoms and an alkoxy group having from 1 to 6 carbon atoms, of which a phenyl group, a 2-fluorophenyl group, a 4-fluorophenyl group, a 2,4-difluorophenyl group, a 2-fluoro-4-hydroxyphenyl group, a 3-amino-4,6-difluorophenyl group and a 4,6-difluoro-3-methylaminophenyl group are preferable.

The heteroaryl group is a substituent derived from a five-membered or six-membered aromatic heterocyclic compound containing one or more hetero-atoms selected from a nitrogen atom, an oxygen atom and a sulfur atom. As examples of the heteroaryl group of substituent $R^1$, a pyridyl group and a pyrimidyl group can be cited. An alkyl group and a halogen atom, for example, are preferable as the substituents on these rings. A 6-amino-3,5-difluoro-2-pyridyl group is particularly preferable.

A methoxy group is preferable as the alkoxy group having from 1 to 6 carbon atoms. A methylamino group is preferable as the alkylamino group having from 1 to 6 carbon atoms.

As the substituent $R^1$, a halogenocycloalkyl group is preferred, and a 2-halogenocyclopropyl group is more preferred. As the halogen atom, a fluorine atom is preferable.

The substituent $R^2$ is a hydrogen atom or an alkylthio group having from 1 to 6 carbon atoms, or $R^2$ and $R^1$ may be combined to form a hydrocarbon cyclic structure together with the carbon atom and nitrogen atom, to which they are bonded. The thus formed ring may contain a sulfur atom as a constituting atom, and this ring may further have an alkyl group having from 1 to 6 carbon atoms as a substituent. The ring to be formed may have a size of from four-membered ring to six-membered ring, and this ring may be in a saturated, partially saturated or unsaturated form. The following can be cited as the condensed ring structure formed in this manner.

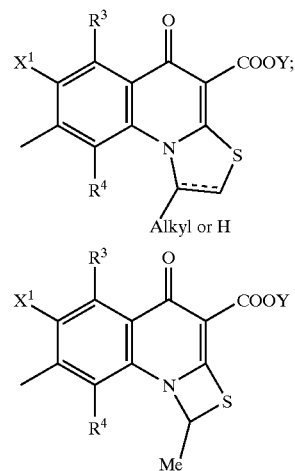

The substituent $X^1$ is a hydrogen atom or a halogen atom, and a fluorine atom is preferable when it is a halogen atom. Among them, a fluorine atom or a hydrogen atom is preferable as the substituent.

The substituent $R^3$ is a hydrogen atom, an amino group, a thiol group, a halogenomethyl group, an alkyl group having from 1 to 6 carbon atoms, an alkenyl group having from 2 to 6 carbon atoms, an alkynyl group having from 2 to 6 carbon atoms or an alkoxy group having from 1 to 6 carbon atoms, wherein the amino group may have one or more substituents selected from the group consisting of a formyl group, an alkyl group having from 1 to 6 carbon atoms and an acyl group having from 2 to 5 carbon atoms.

The alkyl group is a straight chain or branched chain group having from 1 to 6 carbon atoms, preferably a methyl group, an ethyl group, a n-propyl group or an isopropyl group. The alkenyl group is a straight chain or branched chain group having from 2 to 6 carbon atoms, preferably a vinyl group. The alkynyl group is a straight chain or branched chain group having from 2 to 6 carbon atoms, preferably an ethynyl group. As the halogen of halogenomethyl group, a fluorine atom is particularly preferable, and its number is from 1 to 3. As the alkoxy group, it may have from 1 to 6 carbon atoms, and an methoxy group is preferable.

The substituent $R^3$ is preferably a hydrogen atom, an alkyl group or an amino group, of which a methyl group or an unsubstituted amino group is preferable.

When the substituent $R^3$ is an amino group or a thiol group, it may be protected with a usually used protective group.

Examples of the protective group include a (substituted) alkoxycarbonyl group such as a tert-butoxycarbonyl group or a 2,2,2-trichloroethoxycarbonyl group; a (substituted) aralkyloxycarbonyl group such as a benzyloxycarbonyl group, a p-methoxybenzyloxycarbonyl group or a p-nitrobenzyloxycarbonyl group; a (substituted) acyl group such as an acetyl group, a methoxyacetyl group, a trifluoroacetyl group, a chloroacetyl group, a pivaloyl group, a formyl group or a benzoyl group; a (substituted) alkyl group or a (substituted) aralkyl group such as a tert-butyl group, a benzyl group, a p-nitrobenzyl group, a p-methoxybenzyl group or a triphenylmethyl group; (substituted) ethers such as a methoxymethyl group, a tert-butoxymethyl group, a tetrahydropyranyl group and a 2,2,2-trichloroethoxymethyl group; and (alkyl and/or aralkyl)-substituted silyl groups such as a trimethylsilyl group, an isopropyldimethylsilyl group, a tert-butyldimethylsilyl group, a tribenzylsilyl group and a tert-butyldiphenylsilyl group. Compounds having certain substituents protected with these substituents are particularly preferable as production intermediates (the term "(substituted)" as used herein means that it may have a substituent).

$R^4$ is a hydrogen atom, an amino group, a halogen atom, a cyano group, a halogenomethyl group, a halogenomethoxy group, an alkyl group having from 1 to 6 carbon atoms, an alkenyl group having from 2 to 6 carbon atoms, an alkynyl group having from 2 to 6 carbon atoms or an alkoxy group having from 1 to 6 carbon atoms, wherein the amino group may have one or more substituents selected from the group consisting of a formyl group, an alkyl group having from 1 to 6 carbon atoms and an acyl group having from 2 to 5 carbon atoms.

The alkyl group is a straight chain or branched chain group having from 1 to 6 carbon atoms, preferably a methyl group, an ethyl group, a n-propyl group or an isopropyl group. The alkenyl group is a straight chain or branched chain group having from 2 to 6 carbon atoms, preferably a vinyl group. The alkynyl group is a straight chain or branched chain group having from 2 to 6 carbon atoms, preferably an ethynyl group. As the halogen of halogenomethyl group, a fluorine atom is particularly preferable, and its number may be from 1 to 3. As the alkoxy group, it may have from 1 to 6 carbon atoms, and a methoxy group is preferable. As the halogen of halogenomethoxy group, a fluorine atom is particularly preferable, and its number may be from 1 to 3.

Among these substituents, alkyl groups or alkoxy groups are preferably. More preferred are a methyl group and an ethyl group.

In addition, this $R^4$ and the $R^1$ described in the foregoing may be combined to form a hydrocarbon cyclic structure together with the carbon atom and nitrogen atom, to which they are bonded, (the ring has a size of from four-membered ring to seven-membered ring, which may be in a saturated, partially saturated or unsaturated form), and the thus formed ring may contain an oxygen atom, a nitrogen atom or a sulfur atom as a constituting atom and may further have an alkyl group having from 1 to 6 carbon atoms as a substituent. The following structures can be exemplified as the condensed ring structure formed in this manner.

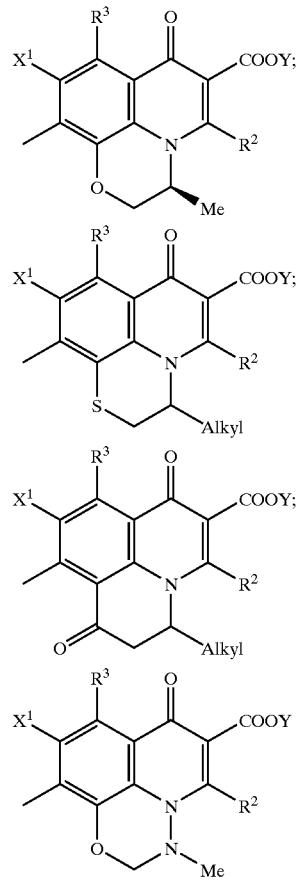

Among these condensed ring systems, 2,3-dihydro-7-oxo-7H-pyrido[1,2,3-de][1.4]benzoxazine-6-carboxy-10-yl group, particularly its 3-position (S)-methyl compound, is preferred.

Preferred as the combination of $R^3$ and $R^4$ is a case in which $R^3$ is an amino group, a hydrogen atom or an alkyl group having from 1 to 6 carbon atoms and $R^4$ is an alkyl group having from 1 to 6 carbon atoms, an alkoxy group having from 1 to 6 carbon atoms, a halogenomethoxy group or a hydrogen atom.

More preferred combination is a case in which $R^3$ is an amino group, a hydrogen atom or a methyl group and $R^4$ is a methyl group, a methoxy group, a difluoromethoxy group or a hydrogen atom.

Particularly preferred combination is a case in which $R^3$ is an amino group, a hydrogen atom or a methyl group and $R^4$ is a methyl group or a methoxy group.

For these $R^3$ and $R^4$, a fluorine atom is preferable as $X^1$.

When each of $X^1$ and $X^2$ is a halogen atom, a fluorine atom is particularly preferable as $X^1$.

$X^2$ is a substituent which serves as a leaving group such as a fluorine atom, a chlorine atom, a bromine atom, a substituted or unsubstituted phenylsulfonyl group or a substituted or unsubstituted alkylsulfonyl group having from 1 to 3 carbon atoms.

Y is a group which constitutes a carboxyl group or an carboxy ester. When it is a carboxy ester, the compound is useful as a synthesis intermediate or a prodrug. For example, alkyl esters, benzyl esters, alkoxyalkyl esters, phenylalkyl esters and phenyl esters are useful as synthesis intermediates.

Also, the ester to be used as a prodrug is an ester which is easily hydrolyzed in vivo and thereby forms a free carboxylic acid, and its examples include oxoalkyl esters such as acetoxymethyl ester, pivaloyloxymethyl ester, ethoxycarbonyl ester, choline ester, dimethylaminoethyl ester, 5-indanyl ester, phthalidynyl ester, 5-alkyl-2-oxo-1,3-dioxol-4-ylmethyl ester and 3-acetoxy-2-oxobutyl ester.

In addition, when Y is a group having a structure represented by the following formula:

$R^5$ is a fluorine atom or an acyloxy group having from 2 to 7 carbon atoms. The acyl moiety of the acyloxy group may be either an aliphatic acyl group or an aromatic acyl group. The aliphatic acyl group is any alkylcarbonyl group. A benzoyl group can be cited as the aromatic acyl group. As the acyloxy group of $R^5$, the use of acetyloxy group is most convenient.

The halogenocyclopropyl group of $R^1$ is described. As the halogen atom to be substituted, a fluorine atom and a chlorine atom can be exemplified, and a fluorine atom is particularly preferable.

As the stereochemical environment of this moiety, regarding the cyclopropane ring, it is particularly preferable that the halogen atom and pyridone-carboxylic acid moiety are in cis-form. More preferred is a (1R, 2S)-2-fluorocyclopropyl group.

So-called antipode isomers exist merely in this cis-2-halogenopropyl moiety of $R^1$, and strong antibacterial activity and high safety were found in each of them.

On the other hand, the nitrogen-containing basic compound is a compound capable of introducing a basic substituent by a substitution reaction, represented by formula R—H (wherein R is a nitrogen-containing basic substituent in which a nitrogen atom is the binding region).

A compound (A) can be exemplified as a preferred example of the compound of formula (1):

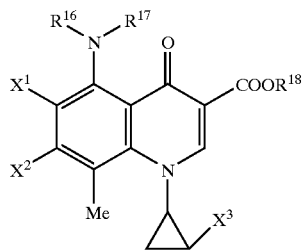

(A)

[In this formula, $X^1$ is a hydrogen atom or a halogen atom, $X^2$ is a halogen atom, $X^3$ is a hydrogen atom or a halogen atom, $R^{16}$ is a hydrogen atom or an acyl group, $R^{17}$ is an acyl group, and $R^{18}$ is a hydrogen atom, an alkyl group having from 1 to 6 carbon atoms or a boron-containing substituent represented by the following formula

(wherein $R^5$ is a halogen atom or an acyloxy group).]

The substituent $R^{16}$ is a hydrogen atom or an acyl group. As the acyl group, it may be either aliphatic or aromatic and may further have an substituent group. Examples of such a substituent include a lower alkyl group and a halogen atom. Examples of the alkyl group include a methyl group, an ethyl group and a propyl group, and examples of the halogen atom include a fluorine atom, a chlorine atom and a bromine atom.

Examples of the acyl group include a formyl group, an acetyl group, a propanoyl group, a butyroyl group, a benzoyl group, a fluoroacetyl group, a difluoroacetyl group, a trifluoroacetyl group, a chloroacetyl group, a dichloroacetyl group and a trichloroacetyl group. Among them, an acetyl group or a substituted acetyl group is preferred, and an acetyl group is most preferred.

$R^{17}$ is an acyl group, and this acyl group can be regarded as the same group of $R^{16}$. When $R^{16}$ and $R^{17}$ are simultaneously acyl groups, they may be the same or different from each other.

$R^{18}$ is a hydrogen atom, a lower alkyl group or a boron-containing substituent represented by the following formula:

(wherein $R^5$ is a halogen atom or an acyloxy group).

When $R^5$ is a lower alkyl group, it may be either a straight chain or a brunched chain group having from 1 to 6 carbon atoms and may further contain a cyclic moiety. Illustrative examples of the alkyl group include a methyl group, an ethyl group and an isopropyl group.

When $R^{18}$ is a boron-containing substituent having the above structure, $R^5$ is preferably a halogen atom or an acyloxy group. As the halogen atom, a fluorine atom is preferred. The acyl group may be any one of the acyl groups exemplified in $R^{16}$ and $R^{17}$. An acetyl group or a substituted acetyl group is preferable as the acyl group. More preferred is an acetyl group. As the boron-containing substituent, a dihalogenoboron group is preferable, and a difluoroboron group is particularly preferable.

Illustrative examples of the mother nucleus of quinolone compounds are shown below:

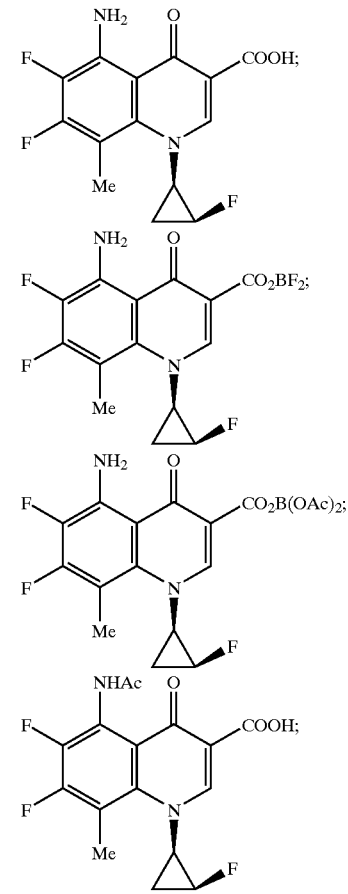

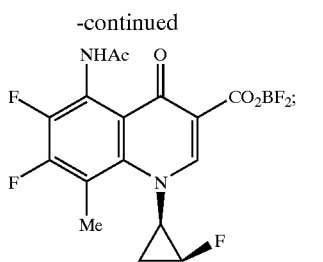
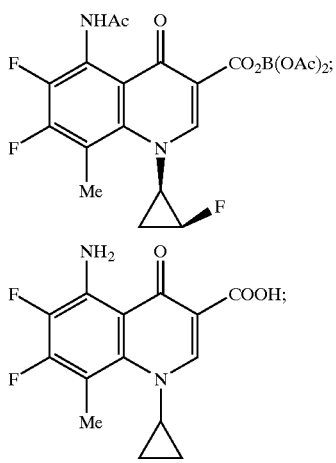
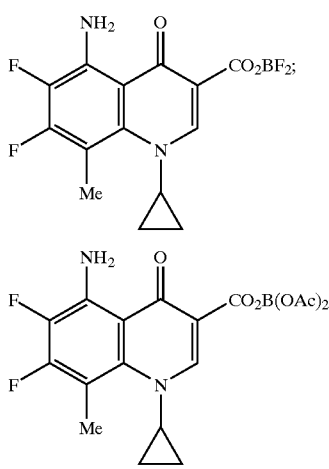
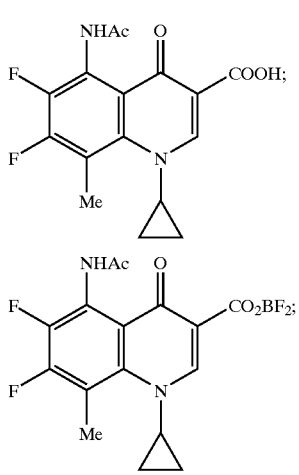

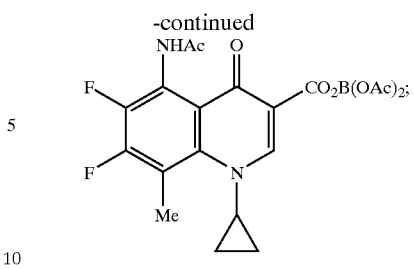

The basic substituent compound (R—H) to be reacted with these compounds is described.

The compound R—H is represented for example by a formula (3):

which is characterized in that $R^6$ and $R^7$ may be the same or different from each other and each represents an optional substituent selected from an alkyl group having from 1 to 6 carbon atoms which may be substituted by an optional substituent selected from the group (halogen, $C_{1-6}$ alkyl group and $C_{1-6}$ alkoxy group), an alkyl group having from 1 to 6 carbon atoms, an aryl group having from 6 to 10 carbon atoms, an aralkyl group having from 7 to 12 carbon atoms, an acyl group having from 1 to 6 carbon atoms, a cycloalkyl group having from 3 to 6 carbon atoms and a hydrogen atom, wherein the cycloalkyl group, aryl group and aralkyl group may become a heterocycle containing one or more hetero-atoms selected from a nitrogen atom, an oxygen atom and a sulfur atom.

Its illustrative examples include amine compounds such as ethylamine, butylamine, diethylamine, isopropylamine, tert-butylamine, diisopropylamine, benzylamine, benzylmethylamine, dibenzylamine, cyclopropylamine, cyclohexylamine and aniline, and compounds in which these unsubstituted compounds are substituted with a substituent optionally selected from the above groups.

Alternatively, $R^6$ and $R^7$ may form a ring together with the nitrogen atom, to which they are bonded, and the formed ring is a monocyclic, bicyclic or tricyclic nitrogen-containing heterocyclic substituent, the heterocyclic substituent may be either in saturated or unsaturated form, may further contain one or more hetero-atoms selected from a nitrogen atom, an oxygen atom and a sulfur atom and may have a bicyclo structure or a spiro cyclic structure, and the heterocyclic substituent has a characteristic in that it may be substituted by one or more optional substituents selected from groups (1), (2) and (3).

Substituent group (1); a $C_{6-10}$ aryl group, a heteroaryl group (five-membered ring or six-membered ring which may contain from 1 to 4 hetero-atoms optionally selected from N, O and S), a $C_{7-12}$ aralkyl group and $C_{6-10}$ heteroaralkyl group (which may contain from 1 to 4 hetero-atoms optionally selected from N, O and S).

Substituent group (2); an amino group, a $C_{1-6}$ alkyl group, a $C_{1-6}$ alkylamino group, a $C_{1-6}$ alkylthio group, a $C_{1-6}$ halogenoalkyl group and a $C_{16}$ aminoalkyl group.

Substituent group (3); a halogen atom, a hydroxyl group, a carbamoyl group and a $C_{1-6}$ alkoxyl group.

Regarding the substituent group (1) which may have a substituent, preferred is at least one optional substituent selected from an alkyl group, an alkoxy group, an alkylthio group, an alkoxycarbonyl group and an acyl group, which are substituted with at least one optional substituent selected from the group A (an amino group, a halogen atom, a hydroxyl group, a carbamoyl group, a $C_{2-6}$ alkyl group, a $C_{2-6}$ alkoxy group, a $C_{2-6}$ alkylamino group, a $C_{2-6}$ alkylthio group, a thiol group, a nitro group, a cyano group, a carboxyl group, a phenyl group, a $C_{2-6}$ alkoxycarbonyl group and a $C_{2-5}$ acyl group) and the group B (a halogen atom, a hydroxyl group, a $C_{1-6}$ alkoxy group and a $C_{1-6}$ alkylthio group).

Regarding the substituent groups (2) and (3) which may have a substituent, preferred is at least one substituent selected from a $C_{1-6}$ alkyl group, a $C_{1-6}$ alkoxy group, a $C_{6-10}$ aryl group and a heteroaryl group (five-membered ring or six-membered ring which may contain from 1 to 4 hetero-atoms optionally selected from N, O and S).

The alkyl group moiety of the substituent group (2) may have a cyclic structure.

The amino group of the substituent group A and the amino group and amino group moiety of the substituent group (2) may have, as 1 or 2 substituents, a $C_{1-6}$ alkyl group (this alkyl group may have a cyclic structure) which may have one or more substituents selected from the group C (a hydroxyl group, a halogen atom, a $C_{1-6}$ alkylthio group and a $C_{1-6}$ alkoxy group) (when the number of alkyl group is 2, they may be the same or different from each other), and may be protected with a protective group.

More preferred is a monocyclic, bicyclic or tricyclic nitrogen-containing heterocyclic substituent in which the nitrogen atom existing in the molecule is the binding position, which is characterized in that
  the nitrogen-containing heterocyclic substituent is in saturated or unsaturated form and may further contain one or more hetero-atoms selected from a nitrogen atom, an oxygen atom and a sulfur atom,
  the nitrogen-containing heterocyclic substituent may also have one or more substituent selected from the group consisting of a halogen atom, an amino group, a hydroxyl group, an alkyl group having from 1 to 6 carbon atoms, a halogenoalkyl group having from 1 to 6 carbon atoms, an aminoalkyl group having from 1 to 6 carbon atoms and an alkylamino group which has 1 or 2 alkyl groups having from 1 to 6 carbon atoms,
  the alkyl group moiety of these alkyl group, halogenoalkyl group, aminoalkyl group and alkylamino group may have a cyclic structure and may have one or more substituents selected from the group consisting of a halogen atom, an alkyl group having from 1 to 6 carbon atoms and an alkoxy group having from 1 to 6 carbon atoms, and
  the amino group and the amino group moiety of amino alkyl group and alkylamino group may be protected with a protective group.

Regarding the cyclic structure which is formed when "the alkyl group moiety has a cyclic structure", its examples include a case in which it binds to the nitrogen-containing heterocyclic substituent by forming a spiro cyclic structure, a case in which it becomes a cycloalkylene group, and one of its bonds binds to the nitrogen-containing heterocyclic substituent and a case in which an alkyl group binds to the nitrogen-containing heterocyclic substituent, and a spiro cyclic structure is formed on the chain or forms a cycloalkyl structure.

The following structures can be exemplified as the substituent R:

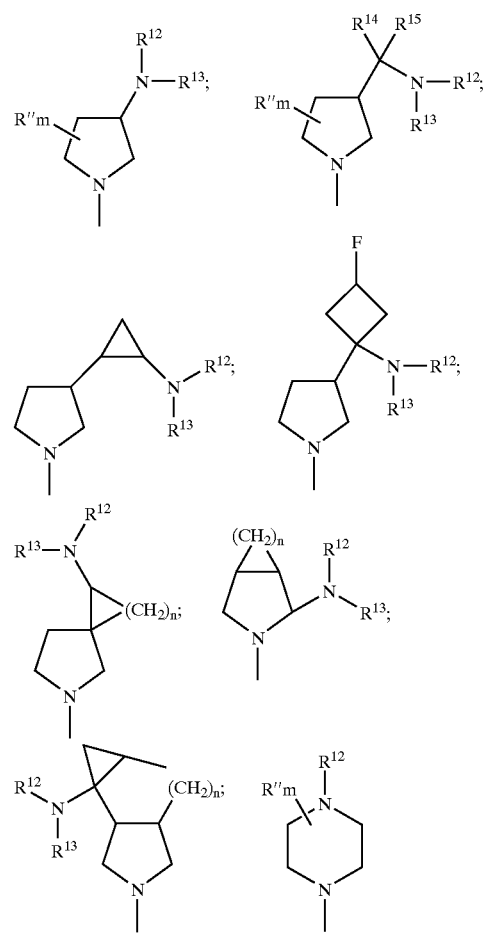

[In the above formulae, each of $R^{12}$ and $R^{13}$ independently represents a hydrogen atom, an alkyl group having from 1 to 6 carbon atoms, a cyclic alkyl group having from 3 to 6 carbon atoms, a halogenoalkyl group having from 1 to 6 carbon atoms, a hydroxyalkyl group having from 1 to 6 carbon atoms or a protective group of amino group, or $R^{12}$ and $R^{13}$ may be combined into a polyalkylene chain having from 2 to 6 carbon atoms and form a cyclic structure by including the nitrogen atom, to which $R^{12}$ and $R^{13}$ are bonded, $R^{14}$ and $R^{15}$ independently represents a hydrogen atom, an alkyl group having from 1 to 6 carbon atoms, a cyclic alkyl group having from 3 to 6 carbon atoms, a halogenoalkyl group having from 1 to 6 carbon atoms or a hydroxyalkyl group having from 1 to 6 carbon atoms, or $R^{14}$ and $R^{15}$ may be combined into a polyalkylene chain having from 2 to 6 carbon atoms and form a cyclic structure by including the carbon atom, to which $R^{14}$ and $R^{15}$ are bonded, R" represents a hydrogen atom, a halogen atom, a hydroxyl group, an alkyl group having from 1 to 6 carbon atoms, a cyclic alkyl group having from 3 to 6 carbon atoms, a halogenoalkyl group having from 1 to 6 carbon atoms, a hydroxyalkyl group having from 1 to 6 carbon atoms or a polyalkylene group having from 2 to 6 carbon atoms (in this case, a cyclic structure is formed by including the atom, to which R" is bonded), and
each of m and n independently represents an integer of from 1 to 4.

Examples of the protective group of amino group include a (substituted) alkoxycarbonyl group such as a tert-butoxycarbonyl group or a 2,2,2-trichloroethoxycarbonyl group; a (substituted) aralkyloxycarbonyl group such as a benzyloxycarbonyl group, a p-methoxybenzyloxycarbonyl group or a p-nitrobenzyloxycarbonyl group; a (substituted) acyl group such as an acetyl group, a methoxyacetyl group, a trifluoroacetyl group, a chloroacetyl group, a pivaloyl group, a formyl group or a benzoyl group; a (substituted) alkyl group or a (substituted) aralkyl group such as a tert-butyl group, a benzyl group, a p-nitrobenzyl group, a p-methoxybenzyl group or a triphenylmethyl group; (substituted) ethers such as a methoxymethyl group, a tert-butoxymethyl group, a tetrahydropyranyl group and a 2,2,2-trichloroethoxymethyl group; and (alkyl and/or aralkyl)-substituted silyl groups such as a trimethylsilyl group, an isopropyldimethylsilyl group, a tert-butyldimethylsilyl group, a tribenzylsilyl group and a tert-butyldiphenylsilyl group.

The following compound (B) can be cited as a preferable compound among the compound (3):

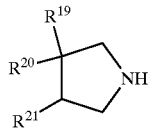

(B)

[In this formula, each of $R^{19}$ and $R^{20}$ independently represents a hydrogen atom, a lower alkyl group or an amino-substituted cyclopropyl group (this amino group may have a substituent or a protective group), or $R^{19}$ and $R^{20}$ may be combined into a group represented by the following formula:

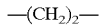

and form a spiro cyclic structure together with the pyrrolidine ring, and $R^{21}$ represents a halogen atom or an amino group which may have a substituent or a protective group.]

$R^{19}$, $R^{20}$ and $R^{21}$ are substituents on the pyrrolidine ring. Among them, each of $R^{19}$ and $R^{20}$ is independently a hydrogen atom, a lower alkyl group or an amino-substituted cyclopropyl group (this amino group may have a substituent or a protective group), or $R^{19}$ and $R^{20}$ may be combined into a group represented by the following formula:

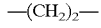

and form a spiro cyclic structure together with the pyrrolidine ring. $R^{21}$ is a halogen atom or an amino group which may have a substituent or a protective group.

When each of $R^{19}$ and $R^{20}$ is a lower alkyl group, it may be either a straight chain or a brunched chain group having from 1 to 6 carbon atoms and may further contain a cyclic moiety. Illustrative examples of the alkyl group include a methyl group, an ethyl group and an isopropyl group.

Each of $R^{19}$ and $R^{20}$ may also be an amino-substituted cyclopropyl group, namely a cyclopropyl group, in which an amino group which may have a substituent or a protective group is substituted on the cyclopropane ring.

The protective group of the amino group on the cyclopropane ring is not particularly limited, with the proviso that it is generally used in this field, and those exemplified in the foregoing may be used.

A lower alkyl group can be cited as the substituent other than protective group, and its examples include similar lower alkyl groups described in the foregoing.

Regarding substitution position of the amino group on the cyclopropyl group, on the carbon atom where cyclopropyl group binds to the 7-position of the quinolone mother nucleus can be cited, though it may be other position than this.

When $R^{21}$ is a halogen atom, it is a fluorine atom or a chlorine atom. Also, when it is an amino group which may have a substituent or a protective group, these substituent and protective group can be regarded as the same case of the amino group when $R^{19}$ or $R^{20}$ is an amino-substituted cyclopropyl group.

Similar to the case of the $R^{19}$, $R^{20}$ and $R^{21}$, $R^{22}$, $R^{23}$ and $R^{24}$ are substituents on the pyrrolidine ring. Different point in the $R^{22}$, $R^{23}$ and $R^{24}$ is that they are amino groups resulting from the elimination of protective groups from the $R^{19}$, $R^{20}$ and $R^{21}$ or they are substituents containing the protective group-eliminated amino group, and the case of other substituents can be considered in the same manner.

The following can be cited as more preferred examples of the substituent R:

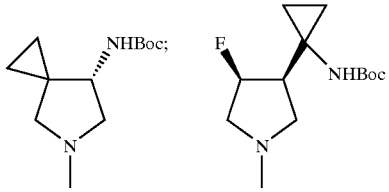

Each step regarding the production method of the invention is described in the following in detail using a 5-amino-8-methylquinolone compound as an example.

A Step for Producing the Compound (A) [from a Compound (E)]

In this step, the amino group of the 5-position (or a corresponding position) of the quinolone skeleton is converted into an acylamino group by an acylation reaction. In this connection, the boron chelation reaction is a reaction in which a boron-containing substituent is introduced into a carboxyl group moiety, which may be an ester, at the 3-position (or a corresponding position), and the present inventors have found that these reactions can be carried out simultaneously. As an example of the starting material of these reactions, a compound of formula (E):

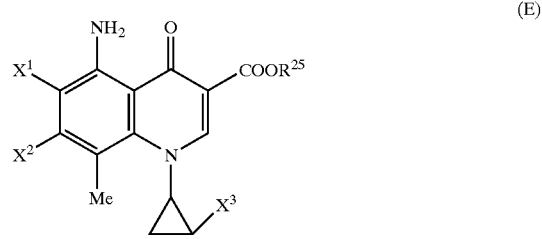

(E)

(wherein $X^1$ is a hydrogen atom or a halogen atom, $X^2$ and $X^3$ are each independently a halogen atom, and $R^{25}$ is a hydrogen atom or an alkyl group having from 1 to 6 carbon atoms) can be used.

An acid anhydride or an acid halide can be used as the acylation agent to be used in the acylation reaction of this step. Examples of the acid anhydride include acetic anhydride, trifluoroacetic anhydride, phenylacetic anhydride, propionic anhydride and benzoic anhydride. Examples of the acid halide include acetyl chloride, acetyl bromide, propionyl chloride and benzoic acid chloride.

The acylation agent is used in an amount of from one equivalent to large excess based on the compound (E). When an acid halide is used, it is preferable to simultaneously use tertiary amines such as triethylamine and pyridine or a nitrogen-containing heterocyclic compound (any one of aromatic, saturated and partially saturated compounds).

When the acylation reaction and boron chelating reaction are simultaneously carried out, it is preferable as an acylation agent to use an acid chloride which does not require a base, and the reactions can be carried out under the above reaction conditions.

As the boron chelating agent to be used for the boron chelating reaction, a boron compound capable of forming a boron chelate with carboxyl group or carbonyl group is used. Illustratively, boron trihalide compounds are used, and ether complexes of these trihaloboron compounds can be used suitably. For example, a boron trifluoride diethyl ether complex and a boron trifluoride tetrahydrofuran complex can be cited. Tetrafluoroboric acid as an analogous compound of trifluoroboron can also be used. By allowing them to undergo the reaction, a dihaloboron group, particularly difluoroboron group can be introduced. Tetrafluoroboric acid is particularly preferable as the agent for simultaneously carrying out both of acylation and boron chelation by the reaction in the presence of an acid anhydride.

As the boron-containing group, it may be not only a halogen-substituted boron group but also an acyloxy-substituted boron group. Introduction of the acyloxyboron group can be carried out by preparing an acyloxyboron chelating reagent in advance from boric acid and an acid anhydride and allowing it to undergo the reaction.

Amount of the boron chelating agent to be used is within the range of from 1 equivalent to 10 equivalents, preferably within the range of from 1 equivalent to 5 equivalents, based on the compound (E).

This reaction can be carried out in a solvent, and any solvent inert to the reaction can be used. Examples of the solvent include an aromatic hydrocarbon solvent such as toluene or xylene; an ester solvent such as ethyl acetate; an ether solvent such as tetrahydrofuran or diethyl ether; a ketone solvent such as acetone or methyl isobutyl ketone; a nitrile solvent such as acetonitrile; an amide solvent such as dimethylformamide, dimethylacetamide or N-methylpyrrolidone; a sulfoxide solvent such as dimethyl sulfoxide; and a chlorine solvent such as dichloromethane or chloroform. In addition, an acylation reagent itself may be used also as the solvent. Particularly, when an acid anhydride is used as the acylation reagent, it is preferable to use it also as the solvent. The solvent may be used in an amount of from 5 to 20 volumes based on the compound (E) (e.g., at a ratio of from 5 ml to 20 ml per 1 g of the compound (E)).

The reaction temperature is within the range of from −30° C. to reflux temperature of the solvent or acylation agent. Also, the reaction time is generally within the range of from 1 to 10 hours.

In this step, there are two ways of selection, namely only the acylation is carried out or the acylation and boron chelation are simultaneously carried out. When the subsequent step in which a basic substituent is introduced into the 7-position is taken into consideration, a compound obtained by simultaneously carrying out the acylation and boron chelation has superior reactivity with the basic substituent compound, so that it is preferable to carry out this reaction. In that case, difluoroboron chelation is preferable as the boron chelation due to easiness of the reaction. That is, it is preferable to carry out the reaction of an acid hydride with dihaloboron chelation agent. Illustratively, it is preferable that the amino group is acetylated by allowing acetic anhydride to react with tetrafluoroboric acid, while difluoroboron group is introduced into the carboxyl group moiety.

A Step in Which a Basic Substituent Compound (R—H) is Allowed to Undergo the Reaction In order to obtain the compound (2), a basic substituent compound

R—H (wherein R is as defined in the foregoing) is allowed to react with the compound (1) under a high pressure in the presence or absence of a solvent. In this case, a base as an acid receptor may be added as occasion demands.

Amount of the basic substituent compound to be used in the production method of the invention is within the range of from 1 to 10 moles, preferably within the range of from 1 to 3 moles, more preferably within the range of from 1 to 1.5 moles, based on 1 mole of the quinolone compound represented by the general formula (1).

The organic solvent to be used in the production method of the invention is not particularly limited, with the proviso that it is inert to the reaction, and its examples include an aromatic hydrocarbon solvent such as toluene or xylene, an ester solvent such as ethyl acetate, an ether solvent such as tetrahydrofuran or diethyl ether, a ketone solvent such as acetone or methyl isobutyl ketone, a nitrile solvent such as acetonitrile, an amide solvent such as dimethylformamide, dimethylacetamide or 1,3-dimethyl-2-imidazolidinone, a sulfoxide solvent such as dimethyl sulfoxide, a sulfone solvent such as sulfolane, and a chlorine solvent such as dichloromethane or chloroform, of which acetonitrile, dimethylformamide, 1,3-dimethyl-2-imidazolidinone, dimethyl sulfoxide and sulfolane are preferable. In this connection, use of the solvent is not necessary in some cases, so that the presence of the reaction solvent is not essential.

Examples of the base as an acid receptor to be used as occasion demands in the production method of the invention generally include organic amines including a trialkylamine, an aryldialkylamine and an (N-substituted) heterocyclic compound, such as triethylamine, N,N-diisopropylethylamine, 1,8-diazabicyclo[5.4.0]-7-undecene, 1,4-diazabicyclo[2.2.2]octane, 1,5-diazabicyclo[4.3.0]-5-nonene and pyridine, and inorganic bases including alkali metal or alkaline earth metal salts of carbonic acid or hydrogen carbonic acid compound, such as sodium carbonate, potassium carbonate, sodium bicarbonate and potassium bicarbonate. Amount of the base to be used may be from the same equivalent to excess amount, but it is general to use up to approximately 3 equivalents.

The reaction of the production method of the invention is carried out at a temperature within a range of up to boiling point of the solvent to be used, with the lower limit of 0° C. and the upper limit of 200° C., but when a boron-chelated quinolone compound is used, the lower limit is 0° C., preferably 40° C., and the upper limit is 80° C., preferably 50° C.

Pressure during the reaction of the production method of the invention is $1 \times 10^7$ Pa, preferably $1.5 \times 10^7$ Pa, as the lower limit, and $5 \times 10^8$ Pa, preferably $3.5 \times 10^8$ Pa, as the upper limit.

The reaction under a high pressure is carried out in a reaction vessel which can sufficiently withstand such a high pressure. The following shows a series of the high pressure reaction steps.

(1) A reaction solution prepared by dissolving the material and necessary agents is transferred into a high pressure reaction vessel, and inside of the high pressure reaction vessel is heated to a predetermined temperature.

(2) After confirming that the temperature became constant, the reaction solution is directly pressurized to a predetermined pressure using a piston connected to a hydraulic pump and hydraulic cylinder.

(3) The reaction is carried out by allowing the solution to stand for a predetermined period of time while keeping the temperature, and then the reaction solution is returned to ordinary pressure and taken out.

Though the reaction time in the production method of the invention is not particularly limited, it is approximately from 3 to 24 hours, but a portion of the material remains in some cases even when the reaction is carried out in this manner. In that case, yield of the product of interest can be improved by once suspending the reaction to recover the material and then subjecting it again to the reaction. According to the method of the invention, decomposition of the material compound can be prevented so that the material compound can be recovered to a recyclable degree, which is useful.

The substitution reaction of the basic substituent compound can be carried out by the following reaction. For example, the compound (C) can be obtained by allowing the compound (A) to react with the compound (B) in the presence or absence of a base, but, in this case, pressurization may not be necessary depending on the structure of $X^3$ and compound (B):

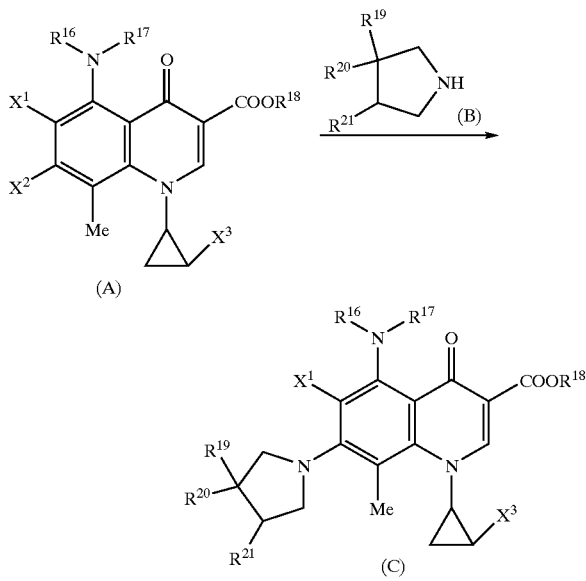

The base to be used may be the same as the above case, and its examples include organic compounds such as a nitrogen-containing heterocyclic compound (aromatic, saturated or partially saturated), a tertiary amine compound and a secondary amine compound (an aromatic hydrocarbon system, an aliphatic system, an aralkyl system and a nitrogen-containing heterocyclic system can be exemplified based on the kind of substituents, and the substituents maybe either a single system or a scramble system of them). In addition to the compounds cited in the foregoing, its illustrative examples include pyridine, 4-dimethylaminopyridine, triethylamine, tributylamine, N-methylpiperidine, DBU, diisopropylamine, dibenzylamine and 2,2,6,6-tetramethylpiperidine. It may also be an inorganic base, and its examples include carbonate, hydroxide or bicarbonate of an alkali metal compound or alkaline earth metal compound, such as potassium carbonate and potassium hydroxide. Also useful as the base are sodium hydride and potassium tert-butoxide as an alkoxide.

The base may be used in an amount of from 1 to 10 equivalents based on the compound (A).

This reaction is generally carried out in a solvent, and any solvent inert to the reaction can be used. Examples of the solvent include an aromatic hydrocarbon solvent such as toluene or xylene; an ester solvent such as ethyl acetate; an ether solvent such as tetrahydrofuran or diethyl ether; a ketone solvent such as acetone or methyl isobutyl ketone; a nitrile solvent such as acetonitrile; an amide solvent such as dimethylformamide, dimethylacetamide or 1,3-dimethyl-2-imidazolidinone; a sulfoxide solvent such as dimethyl sulfoxide; a sulfone solvent such as sulfolane; and a chlorine solvent such as dichloromethane or chloroform. Among them, acetonitrile, dimethylformamide, dimethylacetamide, 1,3-dimethyl-2-imidazolidinone, dimethyl sulfoxide and sulfolane are preferable. These solvent may be used in an amount of approximately from 2 to 50 volumes based on the compound (A).

The reaction temperature is within the range of from 0° C. to reflux temperature of the solvent to be used, preferably within the range of 30° C. to 90° C., but when the compound (A) is a boron-chelated compound, a range of from 30° C. to 50° C. is particularly preferable. Also, the reaction time is generally within the range of from 15 hours to 20 days.

A Step in Which a Compound (D) is Produced from the Compound (C)

A compound (D) can be obtained by hydrolysis reaction of the compound (C). In the hydrolysis reaction of this step, acylated amino group and boron-chelated carboxyl group are respectively converted into amino group and carboxyl group. When a protective group is present, a step for its elimination is also included.

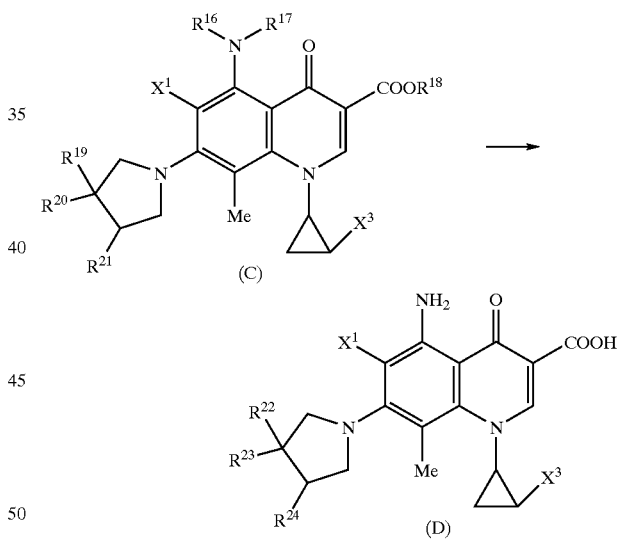

This reaction can be carried out under a known hydrolysis reaction condition such as an acidic condition or an alkaline condition. Examples of the acid to be used in the hydrolysis reaction under an acidic condition include inorganic acids such as hydrochloric acid, hydrobromic acid, sulfuric acid and phosphoric acid and organic acids such as trifluoroacetic acid, p-toluenesulfonic acid, methanesulfonic acid and trifluoromethanesulfonic acid. As the hydrolysis with acid, hydrolysis using an inorganic acid is preferable. Also, examples of the alkali to be used in the hydrolysis reaction under an alkaline condition include sodium hydroxide and potassium hydroxide.

This reaction can be carried out in an aqueous solution of the above acid or alkali but can also be carried out in an organic solvent such as methanol, ethanol or isopropanol or in a water-containing organic solvent, and the solvent is used in an amount of from 5 to 20 volumes based on the compound (C).

The reaction temperature is within the range of from 0° C. to reflux temperature of the solvent to be used. Also, the reaction time is generally within the range of from 1 to 10 hours.

Since an amino group is present in the compound (B) used in the reaction to obtain the compound (C), when this amino group has a protective group, it is necessary to remove this protective group. Removing reaction of the protective group may be carried out at the same time with the above hydrolysis reaction when the same conditions can be used. When deprotection is carried out independently from the hydrolysis reaction, the protective group can be removed by a known method depending on the kind of used protective group.

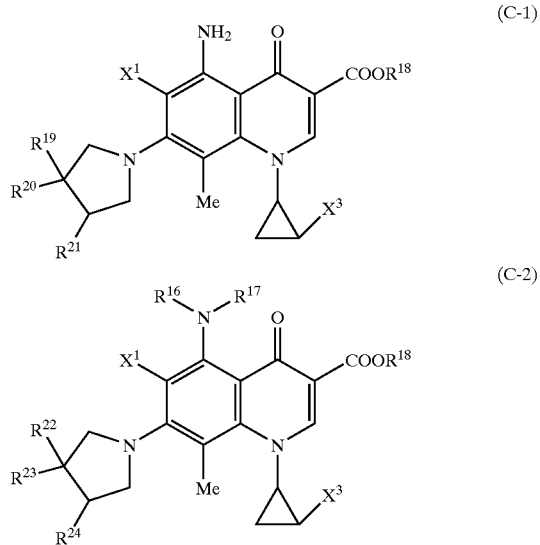

The compound (C-1) is a compound in which an acyl group of the amino group is removed, and the compound (C-2) is a compound in which a protective group on a substituent, particularly the protective group of amino group, is removed. Since the above deprotection reaction can be effected by stepwise removal of protective groups, these compounds can be obtained.

In addition, when $R^{18}$ is an ester, it may be hydrolyzed under an acidic or basic condition. When $R^{18}$ is a boron chelate, it can be converted into carboxylic acid through cleavage of the boron chelate by heat treatment in a protic solvent if necessary in the presence of a base.

BEST MODE FOR CARRYING OUT THE INVENTION

The invention is described further in detail with reference to examples, though the scope of the invention is not limited thereto. Analytical conditions of the high performance liquid chromatography (to be referred to as HPLC hereinafter) in the examples are as follows.
HPLC analysis conditions

CONDITIONS IN COMPARATIVE EXAMPLES 13 and 14 and INVENTIVE Examples 13 and 14

Column: ODS-80TM;
Elution solvent: 0.05 mmol/L $KH_2PO_4$ aqueous solution (pH 3):acetonitrile=40:60 (V/V);
Flow rate: 1.0 ml/min;
Detection wavelength: 275 nm;

CONDITIONS IN COMPARATIVE EXAMPLES 15 to 17 and INVENTIVE Examples 15 to 17

Column: Symmetry C18 5 μm 4.6×150 mm;
Elution solvent: 0.03 mmol/L $KH_2PO_4$ aqueous solution (pH 2.4):acetonitrile=60:40 (V/V);
Flow rate: 1.0 ml/min;
Detection wavelength: 230 nm

INVENTIVE EXAMPLE 1

Ethyl 5-diacetylamino-6,7-difluoro-1-[(1R,2S)-2-fluoro-1-cyclopropyl]-1,4-dihydro-8-methyl-4-oxoquinoline-3-carboxylate A mixture consisting of ethyl 5-amino-6,7-difluoro-1-[(1R,2S)-2-fluoro-1-cyclopropyl]-1,4-dihydro-8-methyl-4-oxoquinoline-3-carboxylate (1.00 g), acetic anhydride (20 ml) and triethylamine (0.94 g) was stirred at an outer temperature of 100° C. for 4 hours. This was concentrated under a reduced pressure, and the resulting crystals were collected by filtration and washed by acetonitrile to obtain 0.90 g (71.7%) of light yellow crystals.

$^1$H-NMR (DMSO-$d_6$) δ: 8.54 (d, J=2.6 Hz, 1 H), 5.23–4.93 (m, 1 H), 4.24 (q, J=7.0 Hz, 3 H), 4.23–4.15 (m, 1 H), 2.63 (d, J=3.0 Hz, 3 H), 2.15 (s, 3 H), 2.08 (s, 3 H), 1.68–1.30 (m, 2 H), 0.91–0.49 (t, J=7.0 Hz, 2 H)

INVENTIVE EXAMPLE 2

[5-Acetylamino-6,7-difluoro-1-[(1R,2S)-2-fluoro-1-cyclopropyl]-1,4-dihydro-8-methyl-4-oxoguinoline-3-carboxylic acid-$O^3$,$O^4$]difluoroboron A mixture consisting of 5-amino-6,7-difluoro-1-[(1R,2S)-2-fluoro-1-cyclopropyl]-1,4-dihydro-8-methyl-4-oxoquinoline-3-carboxylic acid (1.01 g), acetic anhydride (10 ml) and 42% tetrafluoroboric acid (0.72 g) was stirred at room temperature for 1 hour. This was concentrated under a reduced pressure, and ethyl acetate was added to the residue to collect the resulting crystals by filtration. By recrystallizing from an acetone-hexane, 0.37 g (28.9%) of light yellow crystals were obtained.

$^1$H-NMR (DMSO-$d_6$) δ: 10.22 (s, 1 H), 9.39 (d, J=2.6 Hz, 1 H), 5.34–5.05 (m, 1 H), 4.72–4.65 (m, 1 H), 2.81 (d, J=3.3 Hz, 3 H), 2.12 (s, 3 H), 1.88–1.74 (m, 2 H)

INVENTIVE EXAMPLE 3

[5-Diacetylamino-6,7-difluoro-1-[(1R,2S)-2-fluoro-1-cyclopropyl]-1,4-dihydro-8-methyl-4-oxoguinoline-3-carboxylic acid-$O^3$,$O^4$]difluoroboron A mixture consisting of 5-amino-6,7-difluoro-1-[(1R,2S)-2-fluoro-1-cyclopropyl]-1,4-dihydro-8-methyl-4-oxoquinoline-3-carboxylic acid (1.00 g), acetic anhydride (10 ml) and 42% tetrafluoroboric acid (0.73 g) was stirred at an outer temperature of 100° C. for 2 hours. This was concentrated under a reduced pressure, and water was added to the residue to collect the resulting crystals by filtration. By recrystallizing from an acetone-water, 0.50 g (35.0%) of light yellow crystals were obtained.

$^1$H-NMR (DMSO-$d_6$) δ: 9.47 (d, J=2.6 Hz, 1 H), 5.38–5.08 (m, 1 H), 4.82–4.74 (m, 1 H), 2.92 (d, J=3.6 Hz, 3 H), 2.31 (s, 3 H), 1.25 (s, 3 H), 1.92–1.80 (m, 2 H)

INVENTIVE EXAMPLE 4

5-Acetylamino-6,7-difluoro-1-[(1R,2S)-2-fluoro-1-cyclopropyl]-1,4-dihydro-8-methyl-4-oxoguinoline-3-carboxylic acid A mixture consisting of 5-amino-6,7-difluoro-1-[(1R,2S)-2-fluoro-1-cyclopropyl]-1,4-dihydro-8-methyl-4- oxoquinoline-3-carboxylic acid (4.95 g), acetic anhydride (50 ml) and tetrafluoroboric acid (4.30 g) was stirred at room temperature for 1 hour. This was concentrated under a reduced pressure, and ethyl acetate was added to the residue to collect the resulting crystals by filtration. Next, a mixture consisting of the crystals, ethanol (106 ml) and triethylamine (4.2 ml) was stirred at an outer temperature of 80° C. for 30 minutes. This was concentrated under a reduced pressure and acetone was added to the residue to collect the resulting crystals by filtration, thereby obtaining 4.62 g (82.1%) of light yellow crystals.

$^1$H-NMR (DMSO-d$_6$) δ: 10.36 (s, 1 H), 8.81 (d, J=3.0 Hz, 1 H), 5.25–4.99 (m, 1 H), 4.39–4.32 (m, 1 H), 2.70 (d, J=3.3 Hz, 3 H), 2.15 (s, 3 H), 1.73–1.45 (m, 2 H)

INVENTIVE EXAMPLE 5

Ethyl 5-acetylamino-1-cyclopropyl-6,7-difluoro-1,4-dihydro-8-methyl-4-oxoguinoline-3-carboxylate A mixture consisting of ethyl 5-amino-1-cyclopropyl-6,7-difluoro-1,4-dihydro-8-methyl-4-oxoquinoline-3-carboxylate (1.01 g), acetic anhydride (20 ml) and triethylamine (0.95 g) was stirred at an outer temperature of 70° C. for 10 hours. This was cooled with ice and the precipitated crystals were collected by filtration, and the filtrate was further concentrated under a reduced pressure to collect the precipitated crystals by filtration, thereby obtaining 0.90 g (78.8%) of white crystals.

$^1$H-NMR (DMSO-d$_6$) δ: 11.20 (s, 1 H), 8.58 (s, 1 H), 4.27–4.19 (m, 1 H), 4.23 (q, J=6.9 Hz, 2 H), 2.70 (d, J=3.3 Hz, 3 H), 2.14 (s, 3 H), 1.28 (t, J=6.9 Hz, 3 H), 1.18–1.11 (m, 2 H), 0.92–0.86 (m, 2 H)

INVENTIVE EXAMPLE 6

[5-Acetylamino-1-cyclopropyl-6,7-difluoro-1,4-dihydro-8-methyl-4-oxoguinoline-3-carboxylic Acid-O$^3$,O$^4$]difluoroboron A mixture consisting of 5-amino-1-cyclopropyl-6,7-difluoro-1,4-dihydro-8-methyl-4-oxoquinoline-3-carboxylic acid (5.89 g), acetic anhydride (58.9 ml) and 42% tetrafluoroboric acid (5.02 g) was stirred at an outer temperature of 110° C. for 4 hours. This was cooled with ice, and the thus precipitated crystals were collected by filtration and washed with water and acetonitrile to obtain 6.19 g (80.6%) of light yellow crystals.

$^1$H-NMR (DMSO-d$_6$) δ: 10.14 (s, 1 H), 9.30 (s, 1 H), 4.79–4.65 (m, 1 H), 2.89 (d, J=3.6 Hz, 3 H), 2.11 (s, 3 H), 1.33–1.25 (m, 2 H), 1.25–1.16 (m, 2 H)

INVENTIVE EXAMPLE 7

5-Trifluoroacetylamino-1-cyclopropyl-6,7-difluoro-1,4-dihydro-8-methyl-4-oxoguinoline-3-carboxylic acid A mixture consisting of 5-amino-1-cyclopropyl-6,7-difluoro-1,4-dihydro-8-methyl-4-oxoquinoline-3-carboxylic acid (1.47 g) and trifluoroacetic anhydride (7.1 ml) was stirred under ice-cooling for 1 hour. This was mixed with water and the thus precipitated crystals were collected by filtration and washed with water and ethanol to obtain 1.88 g (96.6%) of light yellow crystals.

$^1$H-NMR (DMSO-d$_6$) δ: 14.36 (br s, 1 H), 11.79 (br s, 1 H), 8.86 (s, 1 H), 4.44–4.37 (m, 1 H), 2.82 (d, J=3.6 Hz, 3 H), 1.26–1.19 (m, 2 H), 1.05–1.00 (m, 2 H)

INVENTIVE EXAMPLE 8

5-Acetylamino-7-[(3S,4R)-4-(1-tert-butoxycarbonylaminocyclopropyl)-3-fluoropyrrolidinyl]-6-fluoro-1-[(1R,2S)-2-fluoro-1-cyclopropyl]-1,4-dihydro-8-methyl-4-oxoguinoline-3-carboxylic acid A mixture consisting of 5-acetylamino-6,7-difluoro-1-[(1R,2S)-2-fluoro-1-cyclopropyl]-1,4-dihydro-8-methyl-4-oxoquinoline-3-carboxylic acid (50.2 mg), (3S,4R)-4-(1-tert-butoxycarbonylaminocyclopropyl)-3-fluoropyrrolidine (53.1 mg) and dimethyl sulfoxide (0.25 ml) was stirred at an outer temperature of 80° C. for 38 hours. When quantitative analysis was carried out by a high performance liquid chromatography after completion of the reaction, formed amount of the compound of interest 5-acetylamino-7-[(3S,4R)-4-(1-tert-butoxycarbonylaminocyclopropyl)-3-fluoropyrrolidinyl]-6-fluoro-1-[(1R,2S)-2-fluoro-1-cyclopropyl]-1,4-dihydro-8-methyl-4-oxoquinoline-3-carboxylic acid corresponded to 63.0 mg. The formation ratio was 76.8%.

$^1$H-NMR (DMSO-d$_6$) δ: 10.01 (s, 1 H), 8.69 (d, J=3.0 Hz, 1 H), 7.24 (s, 1 H), 5.39–5.21 (m, 1 H), 5.19–4.96 (m, 1 H), 4.25–4.17 (m, 1 H), 4.09–4.04 (m, 1 H), 3.90–3.78 (m, 1 H), 3.44–3.32 (m, 2 H), 2.78–2.64 (m, 1 H), 2.38 (s, 3 H), 2.10 (s, 3 H), 1.64–1.14 (m, 2 H), 1.38 (s, 9 H), 0.91–6.61 (m, 4 H)

INVENTIVE EXAMPLE 9

5-Acetylamino-7-[(7S)-7-tert-butoxycarbonylamino-5-azaspiro[2.4]hept-5-yl]-1-cyclopropyl-6-fluoro-1,4-dihydro-8-methyl-4-oxoguinoline-3-carboxylic acid A mixture consisting of 5-acetylamino-1-cyclopropyl-6,7-difluoro-1,4-dihydro-8-methyl-4-oxoquinoline-3-carboxylic acid (51.2 mg), (7S)-7-tert-butoxycarbonylamino-5-azaspiro(2.4)heptane (48.2 mg) and dimethyl sulfoxide (0.25 ml) was stirred at an outer temperature of 95° C. for 20 hours. When quantitative analysis was carried out by a high performance liquid chromatography after completion of the reaction, formed amount of the compound of interest 5-acetylamino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid corresponded to 68.9 mg. The formation ratio was 85.6%.

$^1$H-NMR (DMSO-d$_6$) δ: 10.08 (s, 1 H), 8.74 (s, 1 H), 7.32–7.17 (m, 1 H), 4.38–4.20 (m, 1 H), 4.00–3.82 (m, 2 H), 3.77 (d, J=9.6 Hz, 1 H), 3.55–3.42 (m, 1 H), 3.31 (d, J=9.6 Hz, 1 H), 2.51 (s, 3 H), 2.10 (s, 3 H), 1.39 (s, 9 H), 1.34–1.08 (m, 3 H), 0.91–0.49 (m, 5 H)

INVENTIVE EXAMPLE 10

5-Acetylamino-7-[(7S)-7-tert-butoxycarbonylamino-5-azaspiro[2.4]hept-5-yl]-1-cyclopropyl-6-fluoro-1,4-dihydro-8-methyl-4-oxoguinoline-3-carboxylic acid A mixture consisting of [5-acetylamino-1-cyclopropyl-6,7-difluoro-1,4-dihydro-8-methyl-4-oxoquinoline-3-carboxylic acid-O$^3$,O$^4$]difluoroboron (10.8 g), (7S)-7-tert-butoxycarbonylamino-5-azaspiro[2.4]heptane (8.29 g), 1-methylpiperidine (6.64 g) and dimethyl sulfoxide (50 ml) was stirred at an outer temperature of 40° C. for 2 days and then stirred at an outer temperature of 80° C. for 3 days. The reaction solution was mixed with water (200 ml) and extracted with ethyl acetate. Next, the organic layer was washed with 10% citric acid aqueous solution and water and dried over anhydrous sodium sulfate, insoluble material was removed by filtration and then the filtrate was concentrated under a reduced pressure to obtain 17.3 g (purity 76.7%, yield 89.4%) of yellow crystals.

$^1$H-NMR (DMSO-d$_6$) δ: 10.08 (s, 1 H), 8.74 (s, 1 H), 7.32–7.17 (m, 1 H), 4.38–4.20 (m, 1 H), 4.00–3.82 (m, 2 H), 3.77 (d, J=9.6 Hz, 1 H), 3.55–3.42 (m, 1 H), 3.31 (d, J=9.6 Hz, 1 H), 2.51 (s, 3 H), 2.10 (s, 3 H), 1.39 (s, 9 H), 1.34–1.08 (m, 3 H), 0.91–0.49 (m, 5 H)

INVENTIVE EXAMPLE 11

5-Amino-7-[(7S)-7-amino-5-azaspiro[2.4]hept-5-yl]-1-cyclopropyl-6-fluoro-1,4-dihydro-8-methyl-4-oxoquinoline-3-carboxylic acid A 20% sodium hydroxide aqueous solution (169 ml) was added to 84.5% purity 5-acetylamino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid (14.1 g) under stirring at room temperature, and the mixture was stirred at 80° C. for 8 hours. This was extracted with ethyl acetate, the organic layer was washed with saturated ammonium chloride aqueous solution and saturated brine and dried over sodium sulfate, the insoluble matter was removed by filtration, and then the filtrate was concentrated under a reduced pressure to obtain 10.4 g of yellow crystals. A mixture consisting of the crystals (8.87 g), concentrated hydrochloric acid (11 ml) and water (10 ml) was stirred at room temperature for 2 hours. While ice-cooling and stirring, the reaction solution was mixed with 33 g of 30% potassium hydroxide aqueous solution and adjusted to pH 8 with 10% hydrochloric acid. The thus precipitated crystals were collected by filtration, and the filtrate was concentrated under a reduced pressure, mixed with methanol to remove the insoluble matter by filtration and then concentrated under a reduced pressure to obtain crystals. They were combined with the crystals firstly collected by filtration, thereby obtaining 6.89 g (purity 76.2%, yield 71%) of yellow crystals.

$^1$H-NMR (DMSO-$d_6$) δ: 8.61 (s, 1 H), 7.13 (s, 2 H), 6.60–4.60 (br s, 2 H), 4.21–4.06 (m, 1 H), 3.88–3.73 (m, 1 H), 3.61 (d, J=8.6 Hz, 1 H), 3.44 (d, J=8.6 Hz, 1 H), 3.36–3.23 (m, 1 H), 3.20–3.11 (m, 1 H), 2.33 (s, 3 H), 1.25–0.38 (m, 8 H)

INVENTIVE EXAMPLE 12

5-Amino-7-[(7S)-7-amino-5-azaspiro[2.4]hept-5-yl]-1-cyclopropyl-6-fluoro-1,4-dihydro-8-methyl-4-oxoquinoline-3-carboxylic acid A 20% sodium hydroxide aqueous solution (4.8 ml) was added to 76.7% purity 5-acetylamino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid (400.1 mg) under stirring at room temperature, and the mixture was stirred at 80° C. for 5 hours. While stirring at room temperature, the reaction solution was mixed with concentrated hydrochloric acid and stirred for 1 hour. When quantitative analysis was carried out by a high performance liquid chromatography after neutralization of the reaction solution by adding 20% sodium hydroxide aqueous solution, formed amount of the compound of interest 5-amino-7-[(7S)-7-amino-5-azaspiro[2.4]hept-5-yl]-1-cyclopropyl-6-fluoro-1,4-dihydro-8-methyl-4-oxoquinoline-3-carboxylic acid corresponded to 207.2 mg. The formation ratio was 92%.

$^1$H-NMR (DMSO-$d_6$) δ: 8.61 (s, 1 H), 7.13 (s, 2 H), 6.60–4.60 (br s, 2 H), 4.21–4.06 (m, 1 H), 3.88–3.73 (m, 1 H), 3.61 (d, J=8.6 Hz, 1 H), 3.44 (d, J=8.6 Hz, 1 H), 3.36–3.23 (m, 1 H), 3.20–3.11 (m, 1 H), 2.33 (s, 3 H), 1.25–0.38 (m, 8 H)

EXAMPLE 13

5-Acetylamino-7-[(3S,4R)-4-(1-tert-butoxycarbonylaminocyclopropyl)-3-fluoropyrrolidinyl]-6-fluoro-1-[(1R,2S)-2-fluoro-1-cyclopropyl]-1,4-dihydro-8-methyl-4-oxoquinoline-3-carboxylic acid

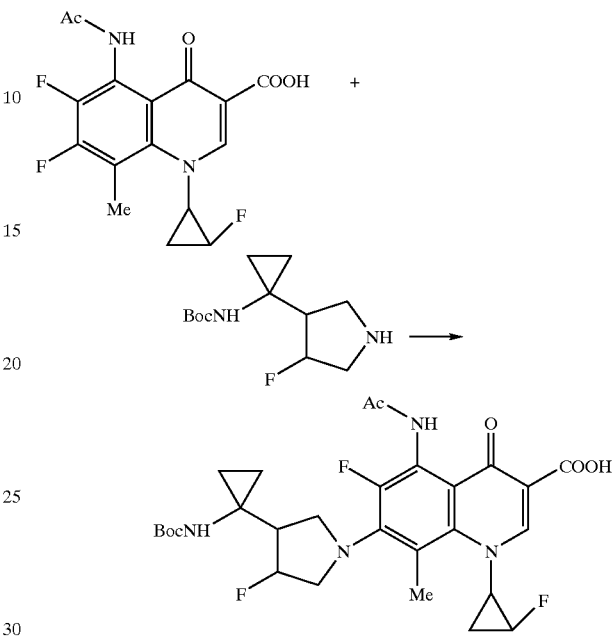

Comparative Example 13

A mixture consisting of 5-acetylamino-6,7-difluoro-1-[(1R,2S)-2-fluoro-1-cyclopropyl]-1,4-dihydro-8-methyl-4-oxoquinoline-3-carboxylic acid (54.4 mg, 0.154 mmol), (3S,4R)-4-(1-tert-butoxycarbonylaminocyclopropyl)-3-fluoropyrrolidine (54.5 mg, 0.223 mmol), 1-methylpiperidine (51.3 mg, 0.517 mmol) and dimethyl sulfoxide (0.25 ml) was stirred at an outer temperature of 80° C. for 7 hours. When analysis was carried out by a high performance liquid chromatography after completion of the reaction, formed ratio of the compound of interest 5-acetylamino-7-[(3S,4R)-4-(1-tert-butoxycarbonylaminocyclopropyl)-3-fluoropyrrolidinyl]-6-fluoro-1-[(1R,2S)-2-fluoro-1-cyclopropyl]-1,4-dihydro-8-methyl-4-oxoquinoline-3-carboxylic acid was 49%. Also, residual ratio of the material was 34%.

$^1$H-NMR (DMSO-$d_6$) δ: 10.01 (s, 1 H), 8.69 (d, J=3.0 Hz, 1 H), 7.24 (s, 1 H), 5.39–5.21 (m, 1 H), 5.19–4.96 (m, 1 H), 4.25–4.17 (m, 1 H), 4.09–4.04 (m, 1 H), 3.90–3.78 (m, 1 H), 3.44–3.32 (m, 2 H), 2.78–2.64 (m, 1 H), 2.38 (s, 3 H), 2.10 (s, 3 H), 1.64–1.14 (m, 2 H), 1.38 (s, 9 H), 0.91–0.61 (m, 4 H)

INVENTIVE EXAMPLE 13

A) A mixture consisting of 5-acetylamino-6,7-difluoro-1-[(1R,2S)-2-fluoro-1-cyclopropyl]-1,4-dihydro-8-methyl-4-oxoquinoline-3-carboxylic acid (2.60 g, 7.34 mmol), (3S,4R)-4-(1-tert-butoxycarbonylaminocyclopropyl)-3-fluoropyrrolidine (2.69 g, 11.0 mmol), 1-methylpiperidine (1.34 ml, 11.1 mmol) and dimethyl sulfoxide (13 ml) was heated at an outer temperature of 80° C. for 7 hours under a condition of 2.94×10$^8$ Pa (converted from 3,000 kgf/cm$^2$). When analysis was carried out by a high performance liquid chromatography after completion of the reaction, formed ratio of the compound of interest 5-acetylamino-7-[(3S,4R)-4-(1-tert-butoxycarbonylaminocyclopropyl)-3-fluoropyrrolidinyl]-6-fluoro-1-[(1R,2S)-2-fluoro-1-cyclopropyl]-1,4-dihydro-8-methyl-4-oxoquinoline-3-carboxylic acid was 72%. Also residual ratio of the material was 11%.

$^1$H-NMR (DMSO-d$_6$) δ: 10.01 (s, 1 H), 8.69 (d, J=3.0 Hz, 1 H), 7.24 (s, 1 H), 5.39–5.21 (m, 1 H), 5.19–4.96 (m, 1 H), 4.25–4.17 (m, 1 H), 4.09–4.04 (m, 1 H), 3.90–3.78 (m, 1 H), 3.44–3.32 (m, 2 H), 2.78–2.64 (m, 1 H), 2.38 (s, 3 H), 2.10 (s, 3 H), 1.64–1.14 (m, 2 H), 1.38 (s, 9 H), 0.91–0.61 (m, 4 H)

B) A dimethyl sulfoxide (15 ml) solution containing 5-acetylamino-6,7-difluoro-1-[(1R,2S)-2-fluoro-1-cyclopropyl]-1,4-dihydro-8-methyl-4-oxoquinoline-3-carboxylic acid (3.0 g, 8.47 mmol), (3S,4R)-4-(1-tert-butoxycarbonylaminocyclopropyl)-3-fluoropyrrolidine (3.19 g, 12.7 mmol) and 1-methylpiperidine (1.54 ml, 12.7 mmol) was heated at an outer temperature of 80° C. for 22 hours under a condition of 2.94×10$^8$ Pa. The reaction solution was washed with ethyl acetate to adjust the total volume to 128 ml and then washed twice with 5% citric acid aqueous solution (30 ml) to separate the organic phase and aqueous phase. The aqueous phase was extracted three times with ethyl acetate, combined with the above organic phase and then extracted three times with 5% potassium hydroxide aqueous solution (30 ml). To the aqueous phase were added chloroform (90 ml) and then 3 N hydrochloric acid until pH became 4, thereby separating the organic phase and aqueous phase. The aqueous phase was extracted twice with chloroform, combined with the above organic phase and then dried over anhydrous sodium sulfate. By evaporating the solvent under a reduced pressure, 5-acetylamino-7-[(3S,4R)-4-(1-tert-butoxycarbonylaminocyclopropyl)-3-fluoropyrrolidinyl]-6-fluoro-1-[(1R,2S)-2-fluoro-1-cyclopropyl]-1,4-dihydro-8-methyl-4-oxoquinoline-3-carboxylic acid (4.92 g, purity 90.0%, yield 89.2%) was obtained as yellow amorphous.

EXAMPLE 14

5-Amino-7-[(3S,4R)-4-(1-tert-butoxycarbonylaminocyclopropyl)-3-fluoropyrrolidinyl]-6-fluoro-1-[(1R,2S)-2-fluoro-1-cyclopropyl]-1,4-dihydro-8-methyl-4-oxoquinoline-3-carboxylic acid

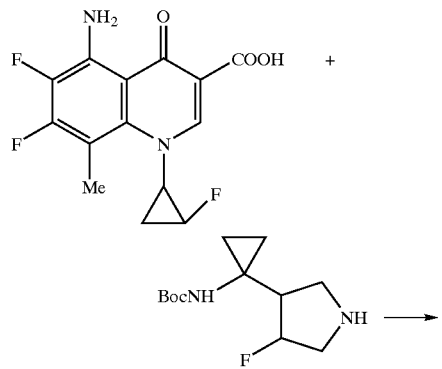

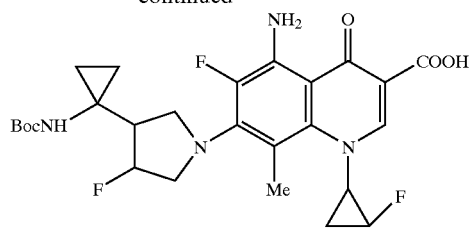

Comparative Example 14

A mixture consisting of 5-amino-6,7-difluoro-1-[(1R,2S)-2-fluoro-1-cyclopropyl]-1,4-dihydro-8-methyl-4-oxoquinoline-3-carboxylic acid (45 mg, 0.144 mmol), (3S,4R)-4-(1-tert-butoxycarbonylaminocyclopropyl)-3-fluoropyrrolidine (52.8 mg, 0.216 mmol), 1-methylpiperidine (18.5 mg, 0.186 mmol) and dimethyl sulfoxide (1.8 ml) was stirred at an outer temperature of 80° C. for 7 hours. When analysis was carried out by a high performance liquid chromatography after completion of the reaction, formed ratio of the compound of interest 5-amino-7-[(3S,4R)-4-(1-tert-butoxycarbonylaminocyclopropyl)-3-fluoropyrrolidinyl]-6-fluoro-1-[(1R,2S)-2-fluoro-1-cyclopropyl]-1,4-dihydro-8-methyl-4-oxoquinoline-3-carboxylic acid was 4%. Also, residual ratio of the starting material was 90%.

$^1$H-NMR (CDCl$_3$) δ: 14.8 (s, 1 H), 8.60 (d, J=3.4 Hz, 1 H), 6.52 (brs, 1 H), 5.28 (dm, J=54.7 Hz, 1 H), 4.85 (dm, J=63.0 Hz, 1 H), 4.11–4.13 (m, 1 H), 3.80–3.88 (m, 2 H), 3.35–3.54 (m, 2 H), 2.30–2.35 (m, 1 H), 2.29 (s, 3 H), 1.45 (s, 9 H), 1.24–1.28 (m, 1 H), 1.00–1.02 (m, 2 H), 0.88–0.90 (m, 1 H), 0.77–0.79 (m, 1 H)

INVENTIVE EXAMPLE 14

A mixture consisting of 5-amino-6,7-difluoro-1-[(1R,2S)-2-fluoro-1-cyclopropyl]-1,4-dihydro-8-methyl-4-oxoquinoline-3-carboxylic acid (0.33 g, 1.06 mmol), (3S,4R)-4-(1-tert-butoxycarbonylaminocyclopropyl)-3-fluoro pyrrolidine (0.39 g, 1.60 mmol), 1-methylpiperidine (0.16 ml, 1.33 mmol) and dimethyl sulfoxide (13 ml) was heated at an outer temperature of 80° C. for 7 hours under a condition of 2.94×10$^8$ Pa. When analysis was carried out by a high performance liquid chromatography after completion of the reaction, formed ratio of the compound of interest 5-acetylamino-7-[(3S,4R)-4-(1-tert-butoxycarbonylaminocyclopropyl)-3-fluoropyrrolidinyl]-6-fluoro-1-[(1R,2S)-2-fluoro-1-cyclopropyl]-1,4-dihydro-8-methyl-4-oxoquinoline-3-carboxylic acid was 17%. Also, residual ratio of the starting material was 79%.

$^1$H-NMR (CDCl$_3$) δ: 14.8 (s, 1 H), 8.60 (d, J=3.4 Hz, 1 H), 6.52 (brs, 1 H), 5.28 (dm, J=54.7 Hz, 1 H), 4.85 (dm, J=63.0 Hz, 1 H), 4.11–4.13 (m, 1 H), 3.80–3.88 (m, 2 H), 3.35–3.54 (m, 2 H), 2.30–2.35 (m, 1 H), 2.29 (s, 3 H), 1.45 (s, 9 H), 1.24–1.28 (m, 1 H), 1.00–1.02 (m, 2 H), 0.88–0.90 (m, 1 H), 0.77–0.79 (m, 1 H)

EXAMPLE 15

5-Acetylamino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid

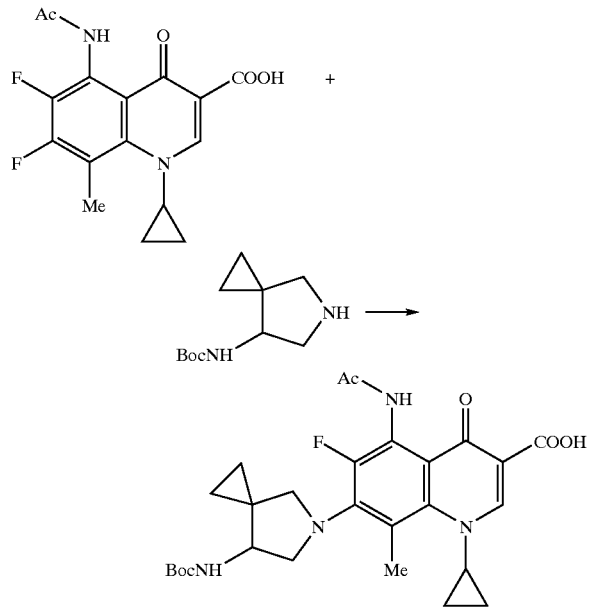

Comparative Example 15

A mixture consisting of 5-acetylamino-1-cyclopropyl-6,7-difluoro-1,4-dihydro-8-methyl-4-oxoquinoline-3-carboxylic acid (48.7 mg, 0.145 mmol), (7S)-7-tert-butoxycarbonylamino-5-azaspiro[2.4]heptane (45.7 mg, 0.215 mmol), triethylamine (30.8 mg, 0.304 mmol) and dimethyl sulfoxide (0.25 ml) was stirred at an outer temperature of 80° C. for 7 hours. When analysis was carried out by a high performance liquid chromatography after completion of the reaction, formed ratio of the compound of interest 5-acetylamino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid was 58%. Also, residual ratio of the starting material was 29%.

$^1$H-NMR (DMSO-$d_6$) δ: 10.08 (s, 1 H), 8.74 (s, 1 H), 7.32–7.17 (m, 1 H), 4.38–4.20 (m, 1 H), 4.00–3.82 (m, 2 H), 3.77 (d, J=9.6 Hz, 1 H), 3.55–3.42 (m, 1 H), 3.31 (d, J=9.6 Hz, 1 H), 2.51 (s, 3 H), 2.10 (s, 3 H), 1.39 (s, 9 H), 1.34–1.08 (m, 3 H), 0.91–0.49 (m, 5 H)

INVENTIVE EXAMPLE 15

A mixture consisting of 5-acetylamino-1-cyclopropyl-6,7-difluoro-1,4-dihydro-8-methyl-4-oxoquinoline-3-carboxylic acid (2.60 g, 7.75 mmol), (7S)-7-tert-butoxycarbonylamino-5-azaspiro[2.4]heptane (2.46 g, 11.6 mmol), triethylamine (1.62 ml, 11.7 mmol) and dimethyl sulfoxide (13 ml) was heated at an outer temperature of 80° C. for 7 hours under a condition of 2.94×10$^8$ Pa. When analysis was carried out by a high performance liquid chromatography after completion of the reaction, formed ratio of the compound of interest 5-acetylamino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid was 77%. Also, residual ratio of the starting material was 10%.

$^1$H-NMR (DMSO-$d_6$) δ: 10.08 (s, 1 H), 8.74 (s, 1 H), 7.32–7.17 (m, 1 H), 4.38–4.20 (m, 1 H), 4.00–3.82 (m, 2 H), 3.77 (d, J=9.6 Hz, 1 H), 3.55–3.42 (m, 1 H), 3.31 (d, J=9.6 Hz, 1 H), 2.51 (s, 3 H), 2.10 (s, 3 H), 1.39 (s, 9 H), 1.34–1.08 (m, 3 H), 0.91–0.49 (m, 5 H)

EXAMPLE 16

5-Acetylamino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid

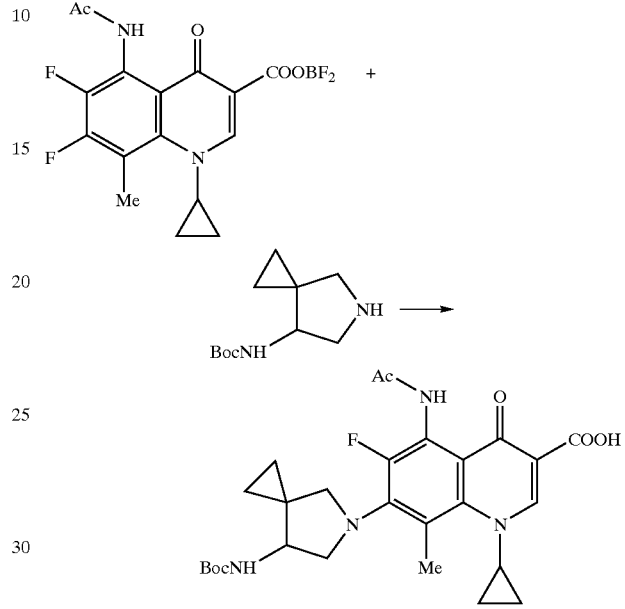

Comparative Example 16

A mixture consisting of [5-acetylamino-1-cyclopropyl-6,7-difluoro-1,4-dihydro-8-methyl-4-oxoquinoline-3-carboxylic acid-O$^3$,O$^4$]difluoroboron (50 mg, 0.130 mmol), (7S)-7-tert-butoxycarbonylamino-5-azaspiro[2.4]heptane (41.5 mg, 0.195 mmol), triethylamine (19.7 mg, 0.195 mmol) and dimethylformamide (4.5 ml) was stirred at an outer temperature of 40° C. for 7 hours. When analysis was carried out by a high performance liquid chromatography after completion of the reaction, formed ratio of the compound of interest 5-acetylamino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid was 11%. Also, residual ration of the starting material was 87%.

$^1$H-NMR (DMSO-$d_6$) δ: 10.08 (s, 1 H), 8.74 (s, 1 H), 7.32–7.17 (m, 1 H), 4.38–4.20 (m, 1 H), 4.00–3.82 (m, 2 H), 3.77 (d, J=9.6 Hz, 1 H), 3.55–3.42 (m, 1 H), 3.31 (d, J=9.6 Hz, 1 H), 2.51 (s, 3 H), 2.10 (s, 3 H), 1.39 (s, 9 H), 1.34–1.08 (m, 3 H), 0.91–0.49 (m, 5 H)

INVENTIVE EXAMPLE 16

A mixture consisting of [5-acetylamino-1-cyclopropyl-6,7-difluoro-1,4-dihydro-8-methyl-4-oxoquinoline-3-carboxylic acid-O$^3$,O$^4$]difluoroboron (0.20 g, 0.521 mmol), (7S)-7-tert-butoxycarbonylamino-5-azaspiro[2.4]heptane (0.17 g, 0.810 mmol), triethylamine (0.11 ml, 0.794 mmol) and dimethylformamide (18 ml) was heated at an outer temperature of 40° C. for 7 hours under a condition of 2.94×10$^8$ Pa. When analysis was carried out by a high performance liquid chromatography after completion of the reaction, formed ratio of the compound of interest 5-acetylamino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid was 32%. Also, residual ratio of the starting material was 51%.

$^1$H-NMR (DMSO-d$_6$) δ: 10.08 (s, 1 H), 8.74 (s, 1 H), 7.32–7.17 (m, 1 H), 4.38–4.20 (m, 1 H), 4.00–3.82 (m, 2 H), 3.77 (d, J=9.6 Hz, 1 H), 3.55–3.42 (m, 1 H), 3.31 (d, J=9.6 Hz, 1 H), 2.51 (s, 3 H), 2.10 (s, 3 H), 1.39 (s, 9 H), 1.34–1.08 (m, 3 H), 0.91–0.49 (m, 5 H)

EXAMPLE 17

5-Amino-7-[(7S)-7-tert-butoxycarbonylamino-5-azaspiro[2.4]hept-5-yl]-1-cyclopropyl-6-fluoro-1,4-dihydro-8-methyl-4-oxoguinoline-3-carboxylic acid

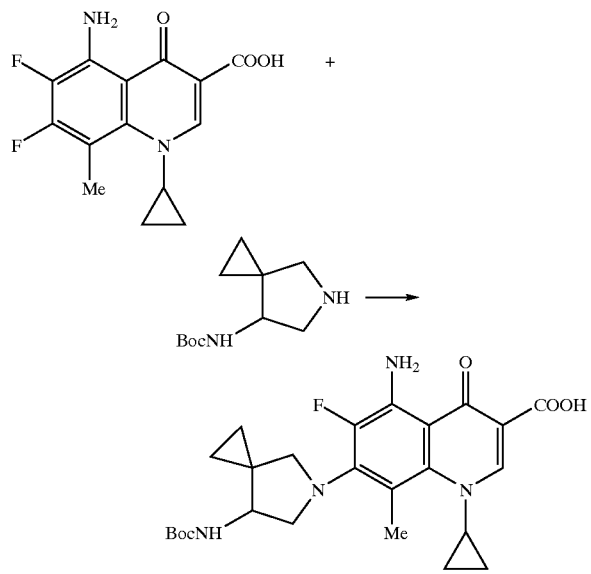

Comparative Example 17

A mixture consisting of 5-amino-1-cyclopropyl-6,7-difluoro-1,4-dihydro-8-methyl-4-oxoquinoline-3-carboxylic acid (50 mg, 0.170 mmol), (7S)-7-tert-butoxycarbonylamino-5-azaspiro[2.4]heptane (108 mg, 0.509 mmol) and dimethyl sulfoxide (4 ml) was stirred at an outer temperature of 80° C. for 7 hours. When analysis was carried out by a high performance liquid chromatography after completion of the reaction, formed ratio of the compound of interest 5-amino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid was 10%. Also, residual ratio of the starting material was 90%.

$^1$H-NMR (DMSO-d$_6$) δ: 8.62 (s, 1 H), 7.20 (s, 1 H), 7.18 (s, 2 H), 4.17–4.14 (m, 1 H), 3.90–3.88 (m, 2 H), 3.71–3.68 (m, 1 H), 3.44–3.42 (m, 1 H), 3.33–3.27 (m, 2 H), 2.35 (s, 3 H), 1.39 (s, 9 H), 1.20–1.09 (m, 2 H), 0.82–0.52 (m, 6 H)

INVENTIVE EXAMPLE 17

A mixture consisting of 5-amino-1-cyclopropyl-6,7-difluoro-1,14-dihydro-8-methyl-4-oxoquinoline-3-carboxylic acid (0.20 g, 0.680 mmol), (7S)-7-tert-butoxycarbonylamino-5-azaspiro[2.4]heptane (0.43 g, 2.03 mmol) and dimethyl sulfoxide (1.6 ml) was heated at an outer temperature of 80° C. for 7 hours under a condition of 2.94×10$^8$ Pa. When analysis was carried out by a high performance liquid chromatography after completion of the reaction, formed ratio of the compound of interest 5-amino-7-[(7S)-7-tert-butoxycarbonylamino-5-azaspiro[2.4]hept-5-yl]-1-cyclopropyl-6-fluoro-1,4-dihydro-8-methyl-4-oxoquinoline-3-carboxylic acid was 35%. Also, residual ratio of the starting material was 63%.

$^1$H-NMR (DMSO-d$_6$) δ: 8.62 (s, 1 H), 7.20 (s, 1 H), 7.18 (s, 2 H), 4.17–4.14 (m, 1 H), 3.90–3.88 (m, 2 H), 3.71–3.68 (m, 1 H), 3.44–3.42 (m, 1 H), 3.33–3.27 (m, 2 H), 2.35 (s, 3 H), 1.39 (s, 9 H), 1.20–1.09 (m, 2 H), 0.82–0.52 (m, 6 H)

REFERENCE EXAMPLES

The compounds (3) and (5) are well known or can be produced easily in accordance with known methods (e.g., JP-A-2-231475, JP-A-8-277284, JP-A-9-67368, WO 97/19072, WO 97/40037, WO 98/02431, WO 98/13370 and WO 98/18783). In addition, some of the compounds are synthesized by the methods shown in Reference Examples, though not limited thereto.

REFERENCE EXAMPLE 1

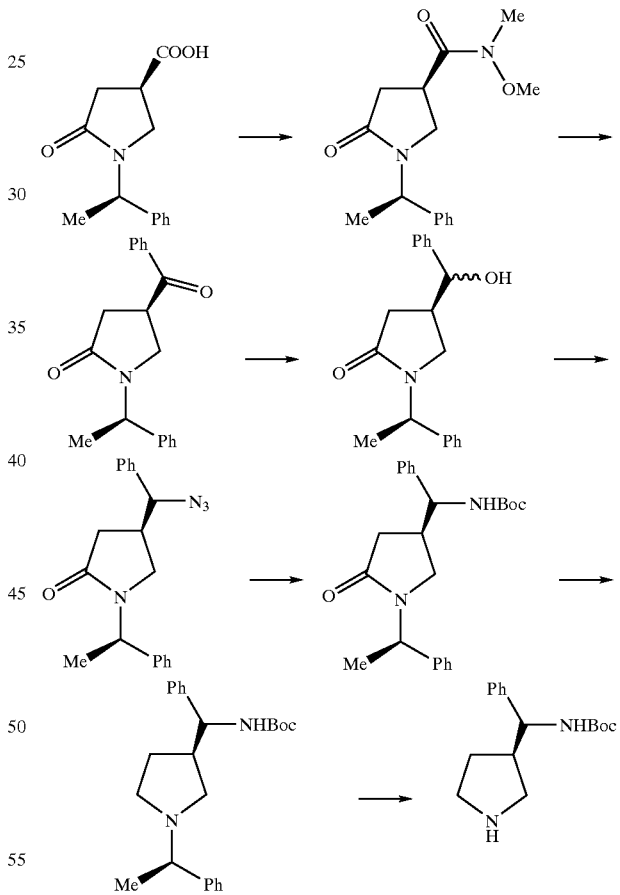

REFERENCE EXAMPLE 1-1

N-Methyl-N-methoxy-1-[1-(R)-phenylethyl]-5-oxopyrrolidine-3-(R)-carboxamide

Oxalyl chloride (6.54 ml, 0.075 mol) and dimethylformamide (3 drops) were added to ice-cooled dichloromethane solution (200 ml) of 1-[1-(R)-phenylethyl]-5-oxopyrrolidine-3-(R)-carboxylic acid (11.66 g, 0.05 mol), and the mixture was stirred overnight at room temperature. After evaporation of the solvent under a reduced pressure, toluene (100 ml) was added and the solvent was again evaporated under a reduced pressure. Dichloromethane (200 ml) and N,O-methylhydroxylamine hydrochloride (5.47 g, 0.055 mol) were added to the resulting residue and, while ice-cooling and stirring, dichloromethane solution (50 ml) of triethylamine (17.4 ml, 0.125 mol) was added dropwise thereto in 15 minutes. After 30 minutes of stirring under ice-cooling, this was stirred at room temperature for 3 hours. The reaction solution was washed with 10% citric acid aqueous solution (100 ml), water (100 ml) and saturated sodium bicarbonate aqueous solution (100 ml) in that order, and then dried over anhydrous sodium sulfate. The solvent was evaporated under a reduced pressure and the residue was subjected to a silica gel column chromatography. By eluting with a chloroform:methanol of from (50:1) to (20:1), 11.32 g (82%) of the title compound was obtained as a brown oil.

$^1$H-NMR (400 MHz, CDCl$_3$) δ: 1.54 (3 H, d, J=6.84 Hz), 2.65 (1 H, dd, J=9.77, 7.09 Hz), 2.77 (1 H, dd, J=8.79, 7.09 Hz), 3.12–3.18 (1 H, m), 3.20 (3 H, s), 3.37–3.48 (1 H, m), 3.55–3.64 (1 H, m), 3.65 (3 H, s), 5.50 (1 H, q, J=6.84 Hz), 7.28–7.37 (5 H, m).

REFERENCE EXAMPLE 1-2

4-(R)-Phenylcarbonyl-1-[1-(R)-phenylethyl]-2-pyrrolidone

In an atmosphere of nitrogen, phenylmagnesium bromide (3 N diethyl ether solution, 15 ml) was added dropwise to tetrahydrofuran solution (50 ml) of N-methyl-N-methoxy-1-[1-(R)-phenylethyl]-5-oxopyrrolidine-3-(R)-carboxamide (2.49 g, 9.0 mmol), and the mixture was stirred at room temperature for 30 minutes. The reaction solution was mixed with 1 N hydrochloric acid (50 ml) under ice-cooling and extracted with ethyl acetate (8 ml×2). The organic layer was washed with saturated brine (100 ml) and dried over anhydrous sodium sulfate. The solvent was evaporated under a reduced pressure and the residue was subjected to a silica gel column chromatography. By eluting with n-hexane:ethyl acetate (1:1), 2.36 g (89%) of the title compound was obtained as a light yellow oil.

$^1$H-NMR (400 MHz, CDCl$_3$) δ: 1.55 (3 H, d, J=6.83 Hz), 2.79 (1 H, dd, J=17.09, 9.77 Hz), 2.81 (1 H, dd, J=17.09, 7.81 Hz), 3.23 (1 H, dd, J=9.76, 8.79 Hz), 3.71 (1 H, dd, J=9.76, 6.35 Hz), 3.97–4.05 (1 H, m), 5.54 (1 H, q, J=6.83 Hz), 7.27–7.38 (5 H, m), 7.42–7.50 (2 H, m), 7.55–7.61 (1 H, m), 7.88–7.90 (2 H, m).

REFERENCE EXAMPLE 1-3

4-(R)-[1-Hydroxy-1-phenylmethyl]-1-[1-(R)-phenylethyl]-2-pyrrolidone [F1], [F2]

Sodium borohydride (280 mg) was added to ice-cooled anhydrous ethanol (40 ml) solution of 4-(R)-phenylcarbonyl-1-[1-(R)-phenylethyl]-2-pyrrolidone (2.17 g, 7.40 mmol), and the mixture was stirred at the same temperature for 1 hour. Under ice-cooling, 10% citric acid (50 ml) was added to the reaction solution and ethanol was evaporated under a reduced pressure. The residue was extracted with chloroform (80 ml×2), and the organic layer was washed with saturated brine (100 ml) and then dried over anhydrous sodium sulfate. The solvent was evaporated under a reduced pressure and the residue was subjected to a silica gel column chromatography. By eluting with n-hexane:ethyl acetate (1:3) to ethyl acetate (100%), 892 mg (41%) of the low polarity title compound [F1] and then 1.163 g (53%) of the high polarity title compound [F2] were obtained each as a light yellow oil.

[F1]; $^1$H-NMR (400 MHz, CDCl$_3$) δ: 1.46 (3 H, d, J=6.84 Hz), 2.03–2.14 (2 H, m), 2.44–2.54 (1 H, m), 3.05–3.09 (1 H, m), 3.36–3.40 (1 H, m), 3.47 (1 H, brs), 4.45 (1 H, d, J=7.81 Hz), 5.38 (1 H, q, J=6.8 Hz), 7.22–7.31 (10 H, m).

[F2]; $^1$H-NMR (400 MHz, CDCl$_3$) δ: 1.37 (3 H, d, J=7.32 Hz), 2.26–2.32 (1 H, m), 2.40–2.55 (2 H, m), 2.73–2.77 (1 H, m), 3.00–3.04 (1 H, m), 4.32 (1 H, brs), 4.42 (1 H d, J=6.8 Hz), 5.33 (1 H, q, J=7.32 Hz), 7.15–7.27 (10 H, m).

REFERENCE EXAMPLE 1-4

4-(R)-[1-Azido-1-phenylmethyl]-1-[1-(R)-phenylethyl]-2-pyrrolidone [F1], [F2]

Under ice-cooling, triethylamine (0.46 ml) and methanesulfonyl chloride (217 μl, 2.80 mmol) were added to dichloromethane (10 ml) solution of 4-(R)-[1-hydroxy-1-phenylmethyl]-1-[1-(R)-phenylethyl]-2-pyrrolidone [F1] (738 mg, 2.50 mmol), and the mixture was stirred at the same temperature for 1 hour. Under ice-cooling, the reaction solution was mixed with 10% citric acid (20 ml) and extracted with chloroform (30 ml×2). The organic layer was washed with saturated brine (100 ml) and then dried over anhydrous sodium sulfate. The solvent was evaporated under a reduced pressure, and the residue was dissolved in N,N-dimethylformamide (10 ml), mixed with sodium azide (488 mg, 7.50 mmol) and then heated at 60° C. for 1.5 hours. After cooling, the reaction solution was mixed with water (50 ml) and extracted with ethyl acetate (70 ml×3). The organic layer was washed with saturated brine (150 ml) and dried over anhydrous sodium sulfate. The solvent was evaporated under a reduced pressure and the residue was subjected to a silica gel column chromatography. By eluting with n-hexane:ethyl acetate (3:2), 701 mg (87%) of the title compound was obtained as a colorless oil.

The same reaction was also carried out on 4-(R)-[1-hydroxy-1-phenylmethyl]-1-[1-(R)-phenylethyl]-2-pyrrolidone [F2] (77%).

[F1]; $^1$H-NMR (400 MHz, CDCl$_3$) δ: 1.46 (3 H, d, J=7.32 Hz), 2.53–2.66 (3 H, m), 2.82 (1 H, dd, J=9.76, 7.81 Hz), 2.94 (1 H, dd, J=9.76, 5.86 Hz), 4.37 (1 H, d, J=7.81 Hz), 5.47 (1 H, q, J=7.32 Hz), 7.21–7.42 (10 H, m).

[F2]; $^1$H-NMR (400 MHz, CDCl$_3$) δ: 1.54 (3 H, d, J=7.33 Hz), 2.14 (1 H, dd, J=17.09, 7.81 Hz), 2.26 (1 H, dd, J=17.09, 8.78 Hz), 2.55–2.65 (1 H, m), 3.14 (1 H, dd, J=10.26, 7.81 Hz), 3.32 (1 H, dd, J=10.26, 6.34 Hz), 4.36 (1 H, d, J=9.28 Hz), 5.49 (1 H, q, J=7.33 Hz), 7.26–7.43 (10 H, m).

REFERENCE EXAMPLE 1-5

4-(R)-[1-tert-Butoxycarbonylamino-1-phenylmethyl]-1-[1-(R)-phenylethyl]-2-pyrrolidone [F1], [F2]

Ethanol (30 ml) solution of 4-(R)-[1-azido-1-phenylmethyl]-1-[1-(R)-phenylethyl]-2-pyrrolidone [F1] (641 mg, 2.0 mmol) was mixed with 10% palladium-carbon catalyst (53.8% moisture, 600 mg) to carry out 6 hours of catalytic hydrogenation at room temperature under ordinary pressure. The reaction solution was filtered, and the solvent was evaporated under a reduced pressure. The residue was dissolved in dichloromethane (20 ml), mixed with di-tert-butyl dicarbonate (655 mg) and triethylamine (560 μl) and stirred at room temperature for 13 hours. The reaction solution was mixed with chloroform (50 ml) and washed with 10% citric acid (8 ml) and water (8 ml), and the organic layer was dried over anhydrous sodium sulfate. The solvent was evaporated under a reduced pressure and the residue was subjected to a silica gel column chromatography. By eluting with an n-hexane:ethyl acetate system of from (1:1) to (2:3), 629 mg (80%) of the title compound was obtained as colorless crystals.

4-(R)-[1-Azido-1-phenylmethyl]-1-[1-(R)-phenylethyl]-2-pyrrolidone [F2] was also subjected to the same reaction (76%).

[F1]; $^1$H-NMR (400 MHz, CDCl$_3$) δ: 1.41 (9 H, s), 1.46 (3 H, d, J=7.32 Hz), 2.47–2.76 (3 H, m), 2.76–2.89 (1 H, m), 2.95–3.08 (1 H, m), 4.62–4.73 (1 H, m), 4.99–5.11 (1 H, m), 5.47 (1 H, q, J=7.32 Hz), 7.20–7.34 (10 H, m).

[F2]; $^1$H-NMR (400 MHz, CDCl$_3$) δ: 1.37 (9 H, s), 1.51 (3 H, d, J=7.32 Hz), 2.08–2.26 (2 H, m), 2.52–2.65 (1 H, m), 3.06–3.18 (1 H, m), 3.24–3.32 (1 H, m), 4.52–4.66 (1 H, m), 5.01–5.11 (1 H, m), 5.47 (1 H, q, J=7.32 Hz), 7.19–7.35 (10 H, m).

REFERENCE EXAMPLE 1-6

3-(R)-[1-tert-Butoxycarbonylamino-1-phenylmethyl]-1-[1-(R)-phenylethyl]pyrrolidine [F1]

In an atmosphere of nitrogen and under ice-cooling, 1 M borane-tetrahydrofuran complex (4.6 ml) was added dropwise to tetrahydrofuran solution (10 ml) of 4-(R)-[1-tert-butoxycarbonylamino-1-phenylmethyl]-1-[1-(R)-phenylethyl]-2-pyrrolidone [α][F1](600 mg, 1.52 mmol), and the mixture was stirred at room temperature for 13 hours. After evaporation of the solvent under a reduced pressure, the residue was mixed with 80% aqueous ethanol (15 ml) and triethylamine (3 ml), and heated under reflux for 5 hours. After spontaneous cooling, the solvent was evaporated under a reduced pressure and chloroform (30 ml) was added to the residue. This was washed with water (10 ml) and saturated brine (10 ml), and dried over anhydrous sodium sulfate. The solvent was evaporated under a reduced pressure and the residue was subjected to a silica gel column chromatography. By eluting with chloroform:methanol (20:1), 510 mg (88%) of the title compound was obtained as colorless crystals.

4-(R)-[1-tert-Butoxycarbonylamino-1-phenylmethyl]-1-[1-(R)-phenylethyl]-2-pyrrolidone [F2] was also subjected to the same reaction (86%).

[F1]; $^1$H-NMR (400 MHz, CDCl$_3$) δ: 1.34 (3 H, d, J=6.35 Hz), 1.47 (9 H, s), 1.60–1.78 (2 H, m), 2.18–2.39 (3 H, m), 2.42–2.54 (1 H, m), 2.83–2.95 (1 H, m), 3.11 (1 H, q, J=6.35 Hz), 4.47–4.57 (1 H, m), 6.06–6.18 (1 H, m), 7.16–7.33 (10 H, m).

[F2]; $^1$H-NMR (400 MHz, CDCl$_3$) δ: 1.41 (3 H, d, J=6.35 Hz), 1.46 (9 H, s), 1.67–1.78 (1 H, m), 1.89–2.02 (1 H, m), 2.04–2.17 (1 H, m), 2.17–2.28 (1 H, m), 2.37–2.50 (2 H, m), 3.01–3.19 (2 H, m), 4.48–4.58 (1 H, m), 6.62–6.73 (1 H, m), 7.07–7.34 (10 H, m).

REFERENCE EXAMPLE 1-7

3-(R)-[1-tert-Butoxycarbonylamino-1-phenylmethyl] pyrrolidine [F1]

Ethanol (20 ml) solution of 3-(R)-[1-tert-butoxycarbonylamino-1-phenylmethyl]-1-[1-(R)-phenylethyl]pyrrolidine [F1] (495 mg, 1.30mmol) was mixed with 10% palladium-carbon catalyst (53.8% moisture, 500 mg), and 4 hours of catalytic hydrogenation was carried out under atmospheric pressure while heating at an outer temperature of 50° C. The reaction solution was filtered and the solvent was evaporated under a reduced pressure to obtain 359 mg (quantitative) of crude product of the title compound as colorless crystals.

3-(R)-[1-tert-Butoxycarbonylamino-1-phenylmethyl]-1-[1-(R)-phenylethyl]pyrrolidine [F2] was also subjected to the same reaction (quantitative).

REFERENCE EXAMPLE 2

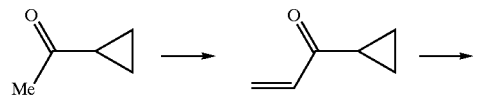

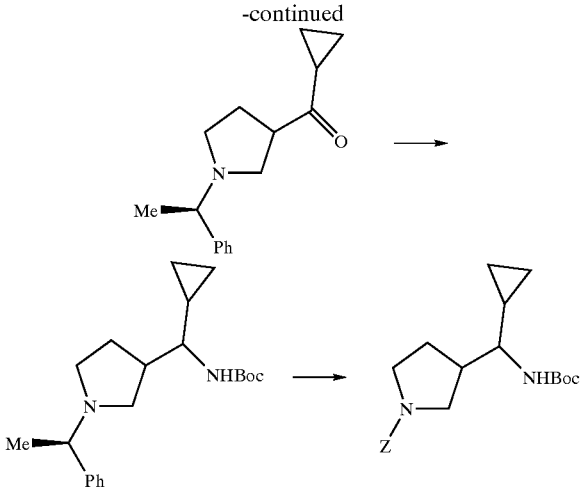

REFERENCE EXAMPLE 2-1

1-Cyclopropyl-2-propen-1-one

Under a stream of nitrogen, cyclopropyl methyl ketone (6.33 g, 75.2 mmol) was dissolved in anhydrous tetrahydrofuran (75 ml). Under ice-cooling and stirring, to this was added dropwise a solution prepared by dissolving N-methylanilinium trifluoroacetate (25.0 g, 113 mmol) in 37% formaldehyde aqueous solution (10.2 ml) under ice-cooling. After the dropwise addition, the reaction solution was heated under reflux for 7 hours. After spontaneous cooling, diethyl ether (100 ml) was added to the reaction solution and stirred, and then the organic layer was separated and collected. The aqueous layer was extracted with diethyl ether (50 ml). Under ice-cooling, saturated sodium bicarbonate aqueous solution (100 ml) was gradually added to the combined organic layer and stirred, and then the organic layer was separated and collected. The thus collected organic layer was washed with saturated brine (100 ml). This was dried over anhydrous magnesium sulfate and then filtered, and the filtrate was concentrated under a reduced pressure of 150 mmHg to obtain a yellow oil containing the title compound. This product was used in the next reaction without purification.

$^1$H-NMR (400 MHz, CDCl$_3$) δ: 0.90–0.96 (2 H, m), 1.08–1.13 (2 H, m), 2.14–2.25 (1 H, m), 5.82 (1 H, dd, J=10.74, 1.47 Hz), 6.29 (1 H, dd, J=17.57, 1.47 Hz), 6.47 (1 H, dd, J=17.57, 10.74 Hz)

REFERENCE EXAMPLE 2-2

Cyclopropyl[1-[1-(R)-phenylethyl]pyrrolidin-3-yl]ketone

The product (8.01 g) containing 1-cyclopropyl-2-propen-1-one described in Reference Example 1 and N-(n-butoxymethyl)-N-[1-(R)-phenylethyl] trimethylsilylmethylamine (23.2 g, 79.9 mmol) were dissolved in dry dichloroethane (350 ml), and trifluoroacetic acid (500 μl) was added dropwise thereto. After 12 hours of stirring at room temperature, the reaction solution was washed with saturated sodium bicarbonate aqueous solution (100 ml) and then with saturated brine (100 ml). After drying over anhydrous magnesium sulfate and subsequent filtration, the filtrate was concentrated under a reduced pressure. The thus obtained residue was subjected to a flash silica gel chromatography, and 9.08 g (49.6%) of the title compound was obtained from an eluate of n-hexane:ethyl acetate=2:1 as a colorless oil component. In this case, this product was obtained as a diastereomer mixture of 1:1.

$^1$H-NMR (400 MHz, CDCl$_3$) δ: 0.83–0.88 (2 H, m), 0.99–1.02 (2 H, m), 1.38 (3 H×½, d, J=2.93 Hz), 1.40

(3H×½, d, J=2.44 Hz), 1.62–1.76 (1 H, m), 1.90–2.17 (2 H, m), 2.35–2.93 (4 H, m), 3.22–3.26 (2 H, m), 7.23–7.34 (5 H, m)

REFERENCE EXAMPLE 2-3
3-[1-(tert-Butoxycarbonyl)amino-1-cyclopropyl]methyl-1-[1-(R)-phenylethyl]pyrrolidine Cyclopropyl[1-[1-(R)-phenylethyl]pyrrolidin-3-yl]ketone (1.563 g, 7.793 mmol) was dissolved in anhydrous methanol (25 ml). To this were added ammonium acetate (5.236 g, 67.93 mmol), sodium cyanoborohydride (435.2 mg, 6.925 mmol) and Molecular Sieves 4A powder (1.86 g), and the mixture was stirred at room temperature for 16 hours under a stream of nitrogen. The reaction solution was filtered through celite and then the solvent was evaporated under a reduced pressure. The residue was dissolved in dichloromethane (100 ml), washed with saturated sodium bicarbonate aqueous solution (50 ml) and saturated brine (50 ml) in that order, and then dried over anhydrous magnesium sulfate. After filtration, the solvent was evaporated under a reduced pressure. The thus obtained residue was dissolved in dry dichloromethane (25 ml) to which, under ice-cooling, was subsequently added dropwise dichloromethane (5 ml) solution of di-tert-butyl dicarbonate (2.225 g, 10.19 mmol). The reaction solution was stirred at room temperature for 2 hours and then concentrated under a reduced pressure. The thus obtained residue was subjected to a flash silica gel chromatography, and 1.299 g (55.5%) of the title compound was obtained from an eluate of chloroform:methanol=10:1 as a colorless oil component.

$^1$H-NMR (400 MHz, CDCl$_3$) δ: 0.20–0.30, 0.35–0.52, 0.68–0.78 (4 H, m), 1.36 (3 H×¼, d, J=5.86 Hz), 1.39 (3H×¾, d, J=5.86 Hz), 1.43 (9 H×¼, s), 1.45 (9 H×¾, s), 1.61–1.74 (1 H, m), 2.25–2.76, 2.80–3.07, 3.18–3.26 (9 H, m), 5.28 (1 H, brs), 7.23–7.34 (5 H, m)

REFERENCE EXAMPLE 2-4
1-Benzyloxycarbonyl-3-[1-(tert-butoxycarbonyl)amino-1-cyclopropyl]methylpyrrolidine (F1, F2, F3, F4)

3-[1-(tert-Butoxycarbonyl)amino-1-cyclopropyl]methyl-1-[1-(R)-phenylethyl]pyrrolidine (1.234 g, 3.582 mmol) was dissolved in dry dichloromethane (20 ml) to which, under ice cooling, was subsequently added dropwise benzyl chloroformate (1,278 μl, 8.955 mmol). After 8 hours of stirring at room temperature, the reaction solution was concentrated under a reduced pressure. The thus obtained residue was subjected to a flash silica gel chromatography, and 959 mg (71.5%) of the title compound was obtained from an eluate of n-hexane:ethyl acetate=2:1 as a colorless oil component.

Next, this product was applied to a fractional HPLC using a chiral column, and four optical isomers F1, F2, F3 and F4 were separated and purified.

HPLC Fractionation Conditions;
Column: CHIRALPAKAD (Daicel Chemical Industries), 2 cm×25 cm
Mobile phase: n-hexane:2-propanol=80:20 (v/v)
Flow rate: 5.0 ml/min
Temperature: room temperature
Detection: UV (254 nm)
Retention Time of Each Isomer
F1: 18 minutes; F2: 23 minutes; F3: 26 minutes; F4: 30 minutes Isomer F1: Colorless Amorphous, 229 mg (17.0%);
$^1$H-NMR (400 MHz, CDCl$_3$) δ: 0.27–0.32 (2 H, m), 0.41–0.45 (1 H, m), 0.54–0.61 (1 H, m), 0.72–0.79 (1 H, m), 1.43 (9 H, s), 1.66–1.78 (1 H, m), 1.99–2.08 (1 H, m), 2.30–2.36 (1 H, m), 2.90–3.03 (1 H, m), 3.12–3.26 (1 H, m), 3.28–3.36 (1 H, m), 3.49–3.72 (2 H, m), 4.50 (1 H, brs), 5.13 (2 H, s), 7.30–7.37 (5 H, m)

Isomer F2: Colorless Amorphous, 96 mg (7.2%);
$^1$H-NMR (400 MHz, CDCl$_3$) δ: 0.29–0.37 (2 H, m), 0.40–0.45 (1 H, m), 0.57–0.62 (1 H, m), 0.76–0.79 (1 H, m), 1.43 (9 H, s), 1.68–1.78 (1 H, m), 2.04–2.09 (1 H, m), 2.36–2.40 (1 H, m), 2.95–3.09 (1 H, m), 3.16 (1 H, t, J=10.74 Hz), 3.31–3.39 (1 H, m), 3.54–3.68 (2 H, m), 4.47 (1 H, brs), 5.13 (2 H, s), 7.29–7.37 (5 H, m)

Isomer F3: Colorless Amorphous, 140 mg (10.4%);
$^1$H-NMR (400 MHz, CDCl$_3$) δ: 0.27–0.39 (2 H, m), 0.41–0.45 (1 H, m), 0.54–0.62 (1 H, m), 0.72–0.80 (1 H, m), 1.43 (9 H, s), 1.66–1.79 (1 H, m), 2.04–2.09 (1 H, m), 2.37–2.40 (1 H, m), 2.95–3.08 (1 H, m), 3.16 (1 H, t, J=10.74 Hz), 3.32–3.39 (1 H, m), 3.54–3.68 (2 H, m), 4.48 (1 H, brs), 5.13 (2 H, s), 7.30–7.37 (5 H, m)

Isomer F4: Colorless Amorphous, 296 mg (22.1%);
$^1$H-NMR (400 MHz, CDCl$_3$) δ: 0.27–0.33 (2 H, m), 0.41–0.45 (1 H, m), 0.54–0.62 (1 H, m), 0.72–0.80 (1 H, m), 1.43 (9 H, s), 1.68–1.78 (1 H, m), 1.99–2.09 (1 H, m), 2.29–2.39 (1 H, m), 2.90–3.03 (1 H, m), 3.12–3.26 (1 H, m), 3.28–3.37 (1 H, m), 3.49–3.73 (2 H, m), 4.50 (1 H, brs), 5.13 (2 H, s), 7.30–7.37 (5 H, m)

Based on the result of the analysis of these $^1$H-NMR data, it was revealed that each of F1 and F4, and F2 and F3, among these four optical isomers has an enantiomer relationship.

REFERENCE EXAMPLE 3

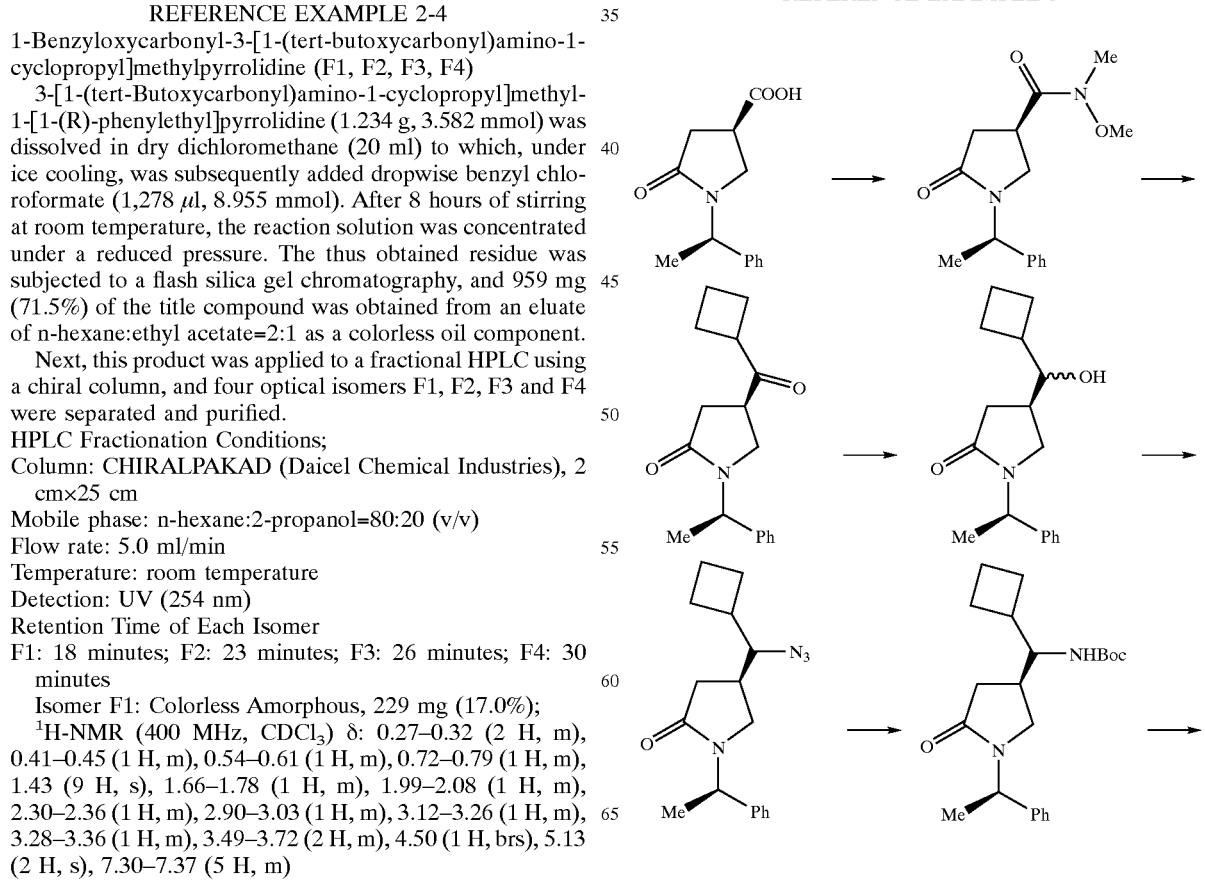

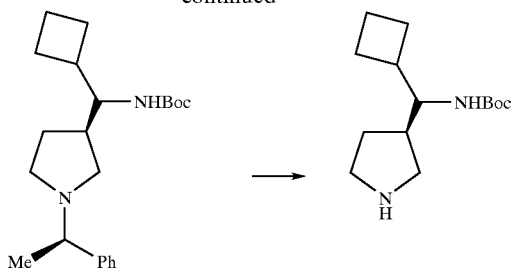

REFERENCE EXAMPLE 3-1
1-[1-(R)-Phenylethyl]-5-oxopyrrolidine-3-(R)—(N-methyl-N-methoxy)carboxamide Under ice-cooling, oxalyl chloride (6.54 ml, 75.0 mmol) and dimethylformamide (3 drops) were added to dichloromethane solution (200 ml) of 1-[1-(R)-phenylethyl]-5-oxopyrrolidine-3-(R)-carboxylic acid (11.7 g, 50.0 mmol), and the mixture was stirred at room temperature for a whole day and night. After evaporation of the solvent under a reduced pressure, toluene (100 ml) was added and the solvent was again evaporated under a reduced pressure. Dichloromethane (200 ml) and N,O-methylhydroxylamine hydrochloride (5.47 g, 55.5 mmol) were added to the resulting residue and, while ice-cooling and stirring, dichloromethane solution (50 ml) of triethylamine (17.4 ml, 125 mmol) was added dropwise thereto spending 15 minutes. After stirring under ice-cooling for 30 minutes, this was further stirred at room temperature for 3 hours. The reaction solution was washed with 10% citric acid aqueous solution (100 ml), water (100 ml) and saturated sodium bicarbonate aqueous solution (100 ml) in that order, and then dried over anhydrous sodium sulfate. The solvent was evaporated under a reduced pressure and the residue was subjected to a silica gel column chromatography to obtain 11.3 g (82%) of the title compound as a brown oil from an eluate of chloroform:methanol=50:1 to 20:1.

$^1$H-NMR (400 MHz, CDCl$_3$) δ: 1.54 (3 H, d, J=6.84 Hz), 2.65 (1 H, dd, J=9.77, 7.09 Hz), 2.77 (1 H, dd, J=8.79, 7.09 Hz), 3.12–3.18 (1 H, m), 3.20 (3 H, s), 3.37–3.48 (1 H, m), 3.55–3.64 (1 H, m), 3.65 (3 H, s), 5.50 (1 H, q, J=6.84 Hz), 7.28–7.37 (5 H, m).

REFERENCE EXAMPLE 3-2
4-(R)-Cyclobutylcarbonyl-1-[1-(R)-phenylethyl]-2-pyrrolidone In an atmosphere of nitrogen, cyclobutylmagnesium chloride (1 N tetrahydrofuran solution, 28 ml) prepared from chlorocyclobutane was added dropwise to tetrahydrofuran solution (50 ml) of 1-[1-(R)-phenylethyl]-5-oxopyrrolidine-3-(R)-(N-methyl-N-methoxy) carboxamide (1.93 g, 7.00 mmol), and the mixture was stirred at room temperature for 30 minutes. The reaction solution was mixed with 1 N hydrochloric acid (50 ml) under ice-cooling and then extracted with ethyl acetate (80 ml×2). The organic layer was washed with saturated brine (100 ml) and dried over anhydrous sodium sulfate. The solvent was evaporated under a reduced pressure and the residue was subjected to a silica gel column chromatography to obtain 1.47 g (78%) of the title compound as a light yellow oil from an eluate of n-hexane:ethyl acetate=1:2.

$^1$H-NMR (400 MHz, CDCl$_3$) δ: 1.53 (3 H, d, J=7.33 Hz), 1.78–1.89 (1 H, m), 1.92–2.06 (1 H, m), 2.06–2.31 (4 H, m), 2.58–2.65 (2 H, m), 3.05 (1 H, dd, J=9.28, 8.79 Hz), 3.13–3.21 (1 H, m), 3.31 (1 H, quint, J=8.30), 3.53 (1 H, dd, J=9.28, 6.83 Hz), 5.48 (1 H, q, J=7.33 Hz), 7.27–7.37 (5 H, m).

REFERENCE EXAMPLE 3-3
4-(R)-(1-Cyclobutyl-1-hydroxy)methyl-1-[1-(R)-phenylethyl]-2-pyrrolidone Under ice-cooling, sodium borohydride (295 mg) was added to ethanol (40 ml) solution of 4-(R)-cyclobutylcarbonyl-1-[1-(R)-phenylethyl]-2-pyrrolidone (2.12 g, 7.80 mmol), and the mixture was stirred at the same temperature for 1 hour. 10% Citric acid (50 ml) was added to the reaction solution under ice-cooling, ethanol was evaporated under a reduced pressure, the residue was extracted with chloroform (80 ml×2), and the organic layer was washed with saturated brine (100 ml) and then dried over anhydrous sodium sulfate. The solvent was evaporated under a reduced pressure and the resulting residue was subjected to a silica gel column chromatography to obtain 2.10 g (98%) of the title compound as a light yellow oil (isomer mixture) from an eluate of n-hexane:ethyl acetate=1:3.

$^1$H-NMR (400 MHz, CDCl$_3$) δ: 1.50 (3 H, d, J=6.83 Hz), 1.68–2.01 (6 H, m), 2.14–2.45 (3 H, m), 2.45–2.56 (1 H, m), 2.91–3.05 (1 H, m), 3.19–3.31 (1 H, m), 3.41–3.49 (1 H, m), 5.42–5.49 (1 H, m), 7.24–7.36 (5 H, m).

REFERENCE EXAMPLE 3-4
4-(R)-(1-Azido-1-cyclobutyl)methyl-1-[1-(R)-phenylethyl]-2-pyrrolidone Under ice-cooling, triethylamine (1.36 ml, 9.80 mmol) and methanesulfonyl chloride (640 µl, 8.30 mmol) were added in that order to dichloromethane (35 ml) solution of 4-(R)-(1-cyclobutyl-1-hydroxy)methyl-1-[1-(R)-phenylethyl]-2-pyrrolidone (2.05 g, 7.50 mmol), and the mixture was stirred at the same temperature for 1 hour. The reaction solution was mixed with 10% citric acid (35 ml) under ice-cooling, and extracted with chloroform (50 ml×2), and the organic layer was washed with saturated brine (150 ml) and then dried over anhydrous sodium sulfate. The solvent was evaporated under a reduced pressure, and the residue was dissolved in N,N'-dimethylformamide (30 ml), mixed with sodium azide (1.46 g, 22.5 mmol) and then stirred at 60° C. for 3 hours. After spontaneous cooling, the reaction solution was mixed with water (150 ml) and extracted with ethyl acetate (150 ml×3), and the organic layer was washed with saturated brine (150 ml) and dried over anhydrous sodium sulfate. The solvent was evaporated under a reduced pressure and the residue was subjected to a silica gel column chromatography to obtain 898 mg (40%) of the low polarity title compound (isomer B1) as a colorless oil from an eluate of n-hexane:ethyl acetate=3:2 and also 847 mg (38%) of the high polarity title compound (isomer B2) as colorless crystals from an eluate of n-hexane:ethyl acetate=2:3.

Isomer B1: $^1$H-NMR (400 MHz, CDCl$_3$) δ: 1.52 (3 H, d, J=6.83 Hz), 1.72–2.01 (5 H, m), 2.07–2.17 (1 H, m), 2.26–2.41 (3 H, m), 2.45–2.56 (1 H, m), 2.98 (1 H, dd, J=9.77, 7.81 Hz), 3.14 (1 H, dd, J=9.77, 7.32 Hz), 3.32 (1 H, dd, J=8.76, 3.91 Hz), 5.47 (1 H, q, J=6.83 Hz), 7.25–7.35 (5 H, m).

Isomer B2: $^1$H-NMR (400 MHz, CDCl$_3$) δ: 1.52 (3 H, d, J=6.83 Hz), 1.75–2.03 (5 H, m), 2.03–2.17 (1 H, m), 2.19–2.38 (2 H, m), 2.40–2.56 (2 H, m), 2 H, m), 2.99 (1 H, dd, J=9.77, 8.30 Hz), 3.14 (1 H, dd, J=9.77, 7.32 Hz), 3.30 (1 H, dd, J=8.30, 6.34 Hz), 5.47 (1 H, q, J=6.83 Hz), 7.25–7.35 (5 H, m).

REFERENCE EXAMPLE 3-5
4-(R)-[1-(tert-butoxycarbonyl)amino-1-cyclobutyl]methyl-1-[1-(R)-phenylethyl]-2-pyrrolidone (Isomer B1)

Ethanol (50 ml) solution of 4-(R)-(1-azido-1-cyclobutyl)methyl-1-[1-(R)-phenylethyl]-2-pyrrolidone (isomer B1)

(835 mg, 2.80 mmol) was mixed with 10% palladium-carbon catalyst (53.8% moisture, 850 mg) to carry out 5 hours of catalytic hydrogenation in an atmosphere of hydrogen at room temperature under atmospheric pressure. The reaction solution was filtered, and the solvent was evaporated under a reduced pressure. The thus obtained residue was dissolved in dichloromethane (20 ml), mixed with di-tert-butyl dicarbonate (917 mg) and triethylamine (780 µl), and stirred at room temperature for 15 hours. The reaction solution was mixed with chloroform (50 ml) and washed with 10% citric acid (80 ml) and water (80 ml), and the organic layer was dried over anhydrous sodium sulfate. The solvent was evaporated under a reduced pressure and the residue was subjected to a silica gel column chromatography to obtain 809 mg (78%) of the title compound as a white amorphous from an eluate of n-hexane:ethyl acetate=3:2 to 1:1.

$^1$H-NMR (400 MHz, CDCl$_3$) δ: 1.44 (9 H, s), 1.48 (3 H, d, J=7.32 Hz), 1.66–1.98 (6 H, m), 2.17–2.43 (4 H, m), 2.94–3.03 (1 H, m), 3.09–3.18 (1 H, m), 3.59–3.68 (1 H, m), 4.46–4.58 (1 H, m), 5.46 (1 H, q, J=7.32 Hz), 7.27–7.35 (5 H, m).

REFERENCE EXAMPLE 3-6

3-(R)-[1-(tert-butoxycarbonyl)amino-1-cyclobutyl]methyl-1-[1-(R)-phenylethyl]-2-pyrrolidine (Isomer B1)

In an atmosphere of nitrogen and under ice-cooling, 1 M borane-tetrahydrofuran complex solution (5.6 ml) was added dropwise to tetrahydrofuran solution (15 ml) of 4-(R)-[1-(tert-butoxycarbonyl)amino-1-cyclobutyl]methyl-1-[1-(R)-phenylethyl]-2-pyrrolidone (isomer B1) (700 mg, 1.88 mmol), and the mixture was stirred at room temperature for 13 hours. After evaporation of the solvent under a reduced pressure, the residue was mixed with 80% aqueous ethanol (15 ml) and triethylamine (3 ml), and heated under reflux for 4 hours. After spontaneous cooling, the solvent was evaporated under a reduced pressure, and the thus obtained residue was mixed with chloroform (30 ml), washed with water (10 ml) and saturated brine (10 ml), and then dried over anhydrous sodium sulfate. The solvent was evaporated under a reduced pressure and the resulting residue was subjected to a silica gel column chromatography to obtain 565 mg (84%) of the title compound as colorless crystals from an eluate of chloroform:methanol=20:1.

$^1$H-NMR (400 MHz, CDCl$_3$) δ: 1.36 (3 H, d, J=6.84 Hz), 1.45 (9 H, s), 1.66–1.95 (7 H, m), 2.05–2.22 (2 H, m), 2.22–2.34 (1 H, m), 2.34–2.45 (2 H, m), 3.15 (1 H, q, J=6.84 Hz), 3.43–3.53 (1 H, m), 4.54–4.62 (1 H, m), 7.21–7.31 (5 H, m).

REFERENCE EXAMPLE 3-7

3-(R)-[1-(tert-butoxycarbonyl)amino-1-cyclobutyl]methylpyrrolidine (Isomer B1)

Ethanol (30 ml) solution of 3-(R)-[1-(tert-butoxycarbonyl)amino-1-cyclobutyl]methyl-1-[1-(R)-phenylethyl]pyrrolidine (isomer B1) (516 mg, 1.44 mmol) was mixed with 10% palladium-carbon catalyst (53.8% moisture, 500 mg), and 5 hours of catalytic hydrogenation was carried out in an atmosphere of hydrogen at an outer temperature of 50° C. under atmospheric pressure. The reaction solution was filtered and the solvent was evaporated under a reduced pressure to obtain 366 mg (quantitative) of the title compound as colorless crystals.

REFERENCE EXAMPLE 4

6-Fluoro-1-[2-(S)-fluoro-1-(R)-cyclopropyl]-1,4-dihydro-8-methoxy-7-(4-methylpiperazin-1-yl)-4-oxoquinoline-3-carboxylic acid 1-Methylpiperazine (1.55 ml, 14.0 mmol) and triethylamine (1.95 ml, 14 mmol) were added to dry dimethyl sulfoxide (18 ml). Thereto was added 6,7-difluoro-1-[2-(S)-fluoro-1-(R)-cyclopropyl]-1,4-dihydro-8-methoxy-4-oxoquinoline-3-carboxylic acid-BF$_2$chelate (3.61 g, 10.0 mmol), and the mixture was stirred at room temperature for 22 hours. After concentration of the reaction solution under a reduced pressure, the residue was suspended in a solution of ethanol:water=9:1 (110 ml), mixed with triethylamine (2 ml) and then heated under reflux for 2 hours. After cooling, the reaction solution was concentrated under a reduced pressure. Concentrated hydrochloric acid (20 ml) was added dropwise to the residue under ice-cooling, and the mixture was stirred at room temperature for 30 minutes. The reaction solution was mixed with 1 N hydrochloric acid (5 ml), and the resulting yellow and acidic aqueous solution was washed with chloroform (50 ml×4) and then adjusted to pH 12.0 with sodium hydroxide aqueous solution. The basic aqueous solution was adjusted to pH 7.4 with 1 N hydrochloric acid and then extracted with chloroform (150 ml×5). After drying with anhydrous sodium sulfate, the solvent was evaporated under a reduced pressure. By recrystallizing and purifying the resulting residue from isopropyl alcohol, 2.98 g (7.58 mmol, 76%) of the title compound was obtained as yellow crystals.

$^1$H-NMR (400 MHz, 0.1N NaOD) δ: 1.37–1.53 (2 H, m), 2.17 (3 H, s), 2.43–2.48 (4 H, m), 3.17–3.22 (4 H, m), 3.63–3.68 (3 H, m), 3.90–3.94 (1 H, m), 4.82 (1 H, dm, J=62.0 Hz), 7.59 (1 H, d, J=12.7 Hz), 8.40 (1 H, s).

IR (KBr disk): 2931, 2841, 2817, 2796, 1898, 1768, 1722, 1622, 1603, 1512, 1462, 1435, 1394, 1315, 1290, 1242, 1227, 1207 cm$^{-1}$ Melting point; 192–194° C.

Elemental analysis data: FW 393.39 for C$_{19}$H$_{21}$F$_2$N$_3$O$_4$ Calcd.: C 58.01%; H 5.38%; N 10.68% Found: C 58.02%; H 5.42%; N 10.41%

REFERENCE EXAMPLE 5

7-(3,5-Cis-dimethylpiperazin-1-yl)-6-fluoro-1-[2-(S)-fluoro-1-(R)-cyclopropyl]-1,4-dihydro-8-methoxy-4-oxoguinoline-3-carboxylic acid Cis-2,6-dimethylpiperazine (1.14 g, 10.0 mmol) and triethylamine (1.05 ml, 7.5 mmol) were added to dry dimethyl sulfoxide (10 ml). Thereto was added 6,7-difluoro-1-[2-(S)-fluoro-1-(R)-cyclopropyl]-1,4-dihydro-8-methoxy-4-oxoquinoline-3-carboxylic acid-BF$_2$ chelate (1.81 g, 5.00 mmol), and the mixture was stirred at room temperature for 5 days. After concentration of the reaction solution under a reduced pressure, the residue was suspended in a solution of ethanol:water=9:1 (50 ml), mixed with triethylamine (1 ml) and then heated under reflux for 3 hours. After cooling, the reaction solution was concentrated under a reduced pressure. Concentrated hydrochloric acid (10 ml) was added dropwise to the residue under ice-cooling, and the mixture was stirred at room temperature for 30 minutes. The reaction solution was mixed with 1 N hydrochloric acid (5 ml), and the resulting yellow and acidic aqueous solution was washed with chloroform (50 ml×4) and then adjusted to pH 12.0 with sodium hydroxide aqueous solution. The basic aqueous solution was adjusted to pH 7.4 with 1 N hydrochloric acid and then extracted with chloroform (150 ml×3). After drying with anhydrous sodium sulfate, the solvent was evaporated under a reduced pressure. By recrystallizing and purifying the resulting residue from ethanol, 1.27 g (3.12 mmol, 62%) of the title compound was obtained as yellow crystals.

$^1$H-NMR (400 MHz, 0.1 N NaOD) δ: 1.06 (3 H, s), 1.07 (3 H, s), 1.50–1.68 (2 H, m), 2.77 (1 H, t, J=11.0 Hz), 2.87 (1 H, t, 10.0 Hz), 2.99–3.06 (2 H, m), 3.28–3.35 (2 H, m), 3.75 (3 H, s), 4.02–4.07 (1 H, m), 4.97 (1 H, dm, J=64.1 Hz), 7.72 (1 H, d, J=12.7 Hz), 8.50 (1 H, s).

Melting point; 129–131° C.

Elemental analysis data: FW 425.43 for $C_{20}H_{23}F_2N_3O_4 \cdot 1H_2O$ Calcd.: C 56.46%; H 5.92%; N 9.88% Found: C 56.72%; H 5.92%; N 9.85%

Industrial Applicability

Effects of the invention can be enumerated as follows.

Since the reaction according to the production method of the invention is carried out within a shorter period of time by pressurizing in a closed system, in comparison with the conventional methods (open system), (1) the progress of side reactions (illustratively, decomposition reaction of the quinolone compound as a raw material and decomposition reaction of the solvent) is inhibited, (2) the inhibition of decomposition of the quinolone compound as a starting material renders possible easy purification of the product of interest, by preventing complex reaction and progress of coloring, (3) the inhibition of decomposition of the quinolone compound as a starting material renders possible further improvement of the yield of the product of interest, by more shorter period of reaction of the remaining quinolone compound, and (4) the remaining quinolone compound as a starting material can be recovered and recycled to the reaction, so that these effects render possible improvement of the yield.

Accordingly, a new method for efficiently introducing an amine substitution as the 7-position substituent of the quinolonecarboxylic acid derivative is provided by the invention.

What is claimed is:

1. A method for producing a compound represented by formula (2):

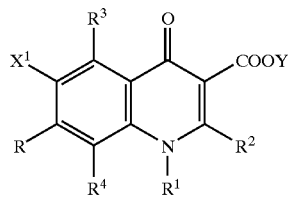

(2)

(wherein $R^1$, $R^2$, $R^3$, $R^4$, R, $X^1$ and Y are as defined in the following), which comprises allowing a compound represented by formula (1):

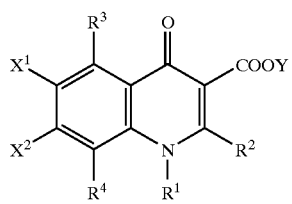

(1)

[wherein $R^1$ represents an alkyl group having from 1 to 6 carbon atoms, an alkenyl group having from 2 to 6 carbon atoms, a halogenoalkyl group having from 1 to 6 carbon atoms, a cyclic alkyl group having from 3 to 6 carbon atoms which may have a substituent, an aryl group which may have a substituent, a heteroaryl group which may have a substituent, an alkoxy group having from 1 to 6 carbon atoms or an alkylamino group having from 1 to 6 carbon atoms, $R^2$ represents a hydrogen atom or an alkylthio group having from 1 to 6 carbon atoms, wherein $R^2$ and $R^1$ may be combined to form a cyclic structure together with the carbon atom and nitrogen atom, to which they are bonded, and this ring may contain a sulfur atom as a constituting atom and may further have an alkyl group having from 1 to 6 carbon atoms as a substituent, $R^3$ represents a hydrogen atom, an amino group, a thiol group, a halogenomethyl group, an alkyl group having from 1 to 6 carbon atoms, an alkenyl group having from 2 to 6 carbon atoms, an alkynyl group having from 2 to 6 carbon atoms or an alkoxy group having from 1 to 6 carbon atoms, wherein the amino group may have one or more substituents selected from the group consisting of a formyl group, an alkyl group having from 1 to 6 carbon atoms and an acyl group having from 2 to 5 carbon atoms, $R^4$ represents a hydrogen atom, an amino group, a halogen atom, a cyano group, a halogenomethyl group, a halogenomethoxy group, an alkyl group having from 1 to 6 carbon atoms, an alkenyl group having from 2 to 6 carbon atoms, an alkynyl group having from 2 to 6 carbon atoms or an alkoxy group having from 1 to 6 carbon atoms, wherein the amino group may have one or more substituents selected from the group consisting of a formyl group, an alkyl group having from 1 to 6 carbon atoms and an acyl group having from 2 to 5 carbon atoms, and $R^4$ and $R^1$ may be combined to form a cyclic structure together with the carbon atom and nitrogen atom, to which they are bonded, and this ring may contain an oxygen atom, a nitrogen atom or a sulfur atom as a constituting atom and may further have an alkyl group having from 1 to 6 carbon atoms as a substituent, $X^1$ represents a hydrogen atom or a halogen atom, $X^2$ represents a halogen atom, and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidynyl group, a 5-alkyl-2-oxo-1,3-dioxol-4-ylmethyl group, a 3-acetoxy-2-oxobutyl group, an alkyl group having from 1 to 6 carbon atoms, an alkoxymethyl group having from 2 to 7 carbon atoms, a phenylalkyl group composed of an alkylene group having from 1 to 6 carbon atoms and phenyl group, or a group of the following formula:

—B($R^5$)$_2$ (wherein $R^5$ represents a fluorine atom or an acyloxy group having from 2 to 7 carbon atoms)] to react with a nitrogen-containing basic compound represented by the following formula:

R—H (wherein R represents a nitrogen-containing basic substituent in which a nitrogen atom is the binding position), under a pressurized condition in a range of $1.5 \times 10^7$ to $3.5 \times 10^8$ Pa in the presence, if necessary, of a base.

2. The production method according to claim 1, wherein the nitrogen-containing basic compound (R—H) is a compound represented by formula (3):

(3)

[wherein $R^6$ and $R^7$ may be the same or different from each other and each represents an optional substituent selected from an alkyl group having from 1 to 6 carbon atoms which may be substituted by an optional substituent selected from groups (halogen, $C_{1-6}$ alkyl group and $C_{1-6}$ alkoxy group), an alkyl group having from 1 to 6 carbon atoms, an aryl group having from 6 to 10 carbon atoms, an aralkyl group having from 7 to 12 carbon atoms, an acyl group having from 1 to 6 carbon atoms, a cycloalkyl group having from 3 to 6 carbon atoms and a hydrogen atom (wherein the cycloalkyl group, aryl group and aralkyl group may become a heterocycle containing one or more hetero-atoms selected from a nitrogen atom, an oxygen atom and a sulfur atom) or $R^6$ and $R^7$ may form a ring together with the nitrogen atom, to which they are bonded, and the formed ring is a monocyclic, bicyclic or tricyclic nitrogen-containing heterocyclic substituent group, the heterocyclic substituent group may be either saturated or unsaturated, may further contain one or more hetero-atoms selected from a nitrogen atom, an oxygen atom and a sulfur atom and may have a bicyclo structure or spiro cyclic structure, and the heterocyclic substituent group may be substituted by one or more optional substituents selected from groups (1), (2) and (3), substituent group (1); a $C_{6-10}$ aryl group, a heteroaryl group (five-membered ring or six-membered ring which may contain from 1 to 4 hetero-atoms optionally selected from N, O and S), a $C_{7-12}$ aralkyl group and a $C_{6-10}$ heteroaralkyl group (which may contain from 1 to 4 hetero atoms optionally selected from N, O and S)
substituent group (2); an amino group, a $C_{1-6}$ alkyl group, a $C_{1-6}$ alkylamino group, a $C_{1-6}$ alkylthio group, a $C_{1-6}$ halogenoalkyl group and a $C_{1-6}$ aminoalkyl group
substituent group (3); a halogen atom, a hydroxyl group, a carbamoyl group and a C.sub.1–6 alkoxyl group (the alkyl group moiety of substituent group (2) may have a cyclic structure)].

3. The production method according to claim 1 or 2, wherein lower limit of the pressure is $1 \times 10^7$ Pa and upper limit of the pressure is $5 \times 10^8$ Pa.

4. The production method according to claim 1 or 2, wherein the compound of formula (I) is a compound represented by formula (A):

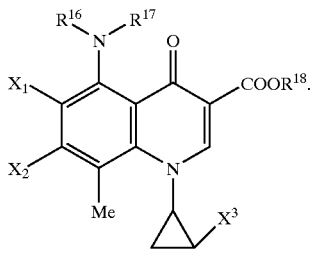
(A)

[wherein $X^1$ represents a hydrogen atom or a halogen atom, $X^2$ represents a halogen atom, $X^3$ represents a hydrogen atom or a halogen atom, $R^{16}$ represents a hydrogen atom or an acyl group, $R^{17}$ represents an acyl group, and $R^{18}$ represents a hydrogen atom, an alkyl group having from 1 to 6 carbon atoms or a boron-containing substituent represented by the following formula:

(wherein $R^5$ represents a halogen atom or an acyloxy group)].

5. The production method according to claim 1 or claim 2, wherein $R^5$ is a halogen atom or an alkylcarbonyloxy group.

6. The production method according to claim 1 or claim 2, wherein $R^5$ is a fluorine atom or an acetyloxy group.

7. The production method according to claim 1 or claim 2, wherein the nitrogen-containing basic compound (R—H) is a compound represented by formula (B):

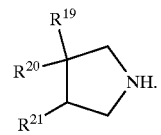
(B)

[wherein each of $R^{19}$ and $R^{20}$ independently represents a hydrogen atom, a lower alkyl group or an amino-substituted cyclopropyl group (this amino group may have a substituent or a protective group), or $R^{19}$ and $R^{20}$ may be combined into a group represented by the following formula:

and form a spiro cyclic structure together with the pyrrolidine ring, and $R^{21}$ represents a halogen atom or an amino group which may have a substituent or a protective group].

8. The production method according to claim 7, wherein $R^{19}$ and $R^{20}$ are a group represented by the following formula:

and $R^{21}$ is an amino group which may have a substituent or a protective group.

9. The production method according to claim 8, wherein the amino group is an amino group of (S)-configuration.

10. The production method according to claim 7, wherein $R^{19}$ is a hydrogen atom, $R^{20}$ is an amino-substituted cyclopropyl group (this amino group may have a substituent or a protective group) and $R^{21}$ is a halogen atom.

11. The production method according to claim 10, wherein $R^{21}$ is a fluorine atom.

12. The production method according to claim 10, wherein $R^{20}$ and $R^{21}$ are in cis-form.

13. The production method according to claim 12, wherein $R^{20}$ is (R)-configuration and $R^{21}$ is (S)-configuration.

* * * * *